US009427229B2

(12) United States Patent  
Gonazles et al.

(10) Patent No.: US 9,427,229 B2  
(45) Date of Patent: Aug. 30, 2016

(54) IMPLANT SYSTEM

(75) Inventors: Donald Gonazles, San Antonio, TX (US); Roger Pisarnwongs, Valencia, CA (US); Tom Weisel, Ventura, CA (US); Jeff Wrana, San Antonio, TX (US)

(73) Assignee: ARTHROCARE CORPORATION, Austin, TX (US)

( * ) Notice: Subject to any disclaimer, the term of this patent is extended or adjusted under 35 U.S.C. 154(b) by 2056 days.

(21) Appl. No.: 12/209,955

(22) Filed: Sep. 12, 2008

(65) Prior Publication Data

US 2009/0099577 A1    Apr. 16, 2009

Related U.S. Application Data

(60) Provisional application No. 60/972,449, filed on Sep. 14, 2007, provisional application No. 61/047,289, filed on Apr. 23, 2008.

(51) Int. Cl.
| | | |
|---|---|---|
| *A61B 17/10* | (2006.01) | |
| *A61B 17/068* | (2006.01) | |
| *A61B 17/064* | (2006.01) | |
| *A61B 17/04* | (2006.01) | |

(52) U.S. Cl.
CPC .......... *A61B 17/068* (2013.01); *A61B 17/064* (2013.01); *A61B 2017/0445* (2013.01); *A61B 2017/0647* (2013.01)

(58) Field of Classification Search
CPC .............. A61B 17/064; A61B 17/068; A61B 2017/0445; A61B 2017/0647
USPC ........................................................ 606/151
See application file for complete search history.

(56) References Cited

U.S. PATENT DOCUMENTS

| | | | |
|---|---|---|---|
| 4,612,933 A | 9/1986 | Brinkerhoff et al. | 227/175.2 |
| 5,389,102 A | 2/1995 | Green et al. | |
| 5,810,240 A | 9/1998 | Robertson | 227/175.2 |
| 5,810,848 A | 9/1998 | Hayhurst | 606/144 |
| 5,827,298 A | 10/1998 | Hart et al. | 606/139 |
| 5,950,633 A | 9/1999 | Lynch et al. | 128/898 |
| 6,074,395 A | 6/2000 | Trott et al. | 606/104 |
| 6,402,766 B2 | 6/2002 | Bowman et al. | 606/151 |
| 6,485,503 B2 | 11/2002 | Jacobs et al. | 606/215 |
| 2,525,183 A1 | 10/2005 | Robison | 606/196 |
| 7,169,163 B2 | 1/2007 | Becker | 606/196 |
| 7,361,168 B2 | 4/2008 | Makower et al. | 604/509 |
| 7,410,480 B2 | 8/2008 | Muni et al. | 604/509 |
| 7,438,208 B2 | 10/2008 | Larson | 227/175.1 |
| 7,547,326 B2 * | 6/2009 | Bhatnagar et al. | 623/17.16 |
| 7,699,870 B2 | 4/2010 | Hart et al. | 606/213 |

(Continued)

OTHER PUBLICATIONS

International Search Report and Written Opinion, issued in International Application No. PCT/US2008/076196, dated Nov. 18, 2008.

(Continued)

*Primary Examiner* — Gregory Anderson  
(74) *Attorney, Agent, or Firm* — Norton Rose Fulbright US LLP

(57) ABSTRACT

A system and method for inserting an implant into soft tissue. The system may include an elongate arm having an implant at a first end of the elongate arm and an actuator at a second end of the elongate arm. The implants may be contained in a cartridge assembly. Methods of inserting an implant may be used during nasal septum reconstruction.

33 Claims, 44 Drawing Sheets

(56) References Cited

U.S. PATENT DOCUMENTS

| | | | |
|---|---|---|---|
| 7,758,594 B2 * | 7/2010 | Lamson et al. | 606/139 |
| 2005/0113850 A1 | 5/2005 | Tagge | 606/151 |
| 2008/0154237 A1 | 6/2008 | Chang et al. | 604/514 |

OTHER PUBLICATIONS

Orlandi and Kennedy, "Revision endoscopic frontal sinus surgery," *Otolaryngologic Clinics of North America*, 34(1): 77-90, Feb. 2001.

* cited by examiner

IMPLANT SYSTEM

CROSS-REFERENCE TO RELATED APPLICATIONS

This application claims priority to U.S. Provisional Patent Application Ser. No. 60/972,449, filed Sep. 14, 2007, and U.S. Provisional Patent Application Ser. No. 61/047,289, filed Apr. 23, 2008, the entire contents of each are expressly incorporated herein by reference.

FIELD OF THE INVENTION

The present disclosure relates generally to systems and methods for inserting implants into a patient's soft tissue. The present disclosure relates more specifically to systems and methods for connecting internal tissues to aid in healing and for approximation of soft tissues during head and neck surgical procedures such as nasal septum reconstruction.

BACKGROUND INFORMATION

In certain medical procedures, it may be desirable to connect internal tissues to aid in healing. One example of such a procedure is nasal septum reconstruction (also known as septoplasty). During a septoplasty, mucoperichondrial flaps are formed on each side of the septum and the deviated cartilage and bone are removed. During the procedure, it is desirable to approximate the flaps to reduce the deadspace and minimize the likelihood of hematoma between the flaps, which may lead to serious complications such as saddle nose deformity.

Existing techniques to approximate the flaps and reduce the deadspace include packing the nasal cavity to bring the flaps into proximity, which can cause high levels of discomfort to the patient and may lead to toxic shock syndrome. More often, the flaps are sutured with a running degradable suture. Suturing in such a small space is very difficult, even for the most highly trained surgeon and can also have complications such as trauma to the lateral wall of the nasal cavity and needle breakage. The use of implants to approximate the flaps and reduce the deadspace near the tissue can reduce patient discomfort and provide for approximation of the soft tissue in specific locations.

SUMMARY

Exemplary embodiments of the present disclosure comprise an implant system comprising: a first elongate arm having a first end and a second end; a cartridge assembly proximal to the first end, wherein the cartridge assembly comprises a plurality of implants; and a handle assembly proximal to the second end, wherein the handle assembly comprises a handle and an actuator. In certain embodiments, the implant system is configured to discharge an implant from the cartridge assembly when the actuator is actuated. The actuator may comprise a trigger, and the actuator may be configured to engage an actuator rod when the actuator is actuated. The actuator rod may be configured to discharge an implant when the actuator is actuated. Certain embodiments may comprise a biasing member configured to bias the actuator rod away from the first end of the first elongate arm. In certain embodiments, the actuator rod may be configured to move generally parallel to the first elongate arm during use, and the actuator rod may comprise a ram configured to engage the actuator during use.

In certain embodiments, the actuator rod may comprise a flexible end proximal to the plurality of implants, and the flexible end of the actuator rod may be configured to engage an implant during use. Certain embodiments may comprise a guide that directs the flexible end of the actuator rod at an angle to the first elongate arm during use, and the guide may be proximal to the first end of the first elongate arm. In certain embodiments, the cartridge assembly may be disposable.

Certain embodiments may comprise a second elongate arm comprising a distal end and a proximal end, and the second elongate arm may be generally parallel to the first elongate arm when the actuator is not actuated. In certain embodiments, the implant system may be configured to move the distal end of the second elongate arm closer to the first end of the first elongate arm when the actuator is actuated. Certain embodiments may comprise a cam gear having a cam surface engaged with the second elongate arm, wherein the actuator comprises an actuator gear engaged with the cam gear, and actuation of the actuator causes the cam surface to move the second elongate arm. Certain embodiments may comprise an actuator having a cam surface engaged with the second elongate arm, wherein actuation of the actuator causes the cam surface to move the second elongate arm. In certain embodiments, the plurality of implants are comprised of an absorbable copolymer.

Certain embodiments of the present disclosure comprise an implant system comprising: an elongate arm having a first end and a second end; an implant proximal to the first end; and an actuator proximal to the second end, wherein the implant system is configured to discharge an implant at an angle to the elongate arm when the actuator is actuated. In certain embodiments, the angle may be between 0 and 180 degrees; more specifically the angle may be between 0 and 90 degrees or more specifically between 0 and 45 degrees. In specific embodiments, the angle may be approximately 90 degrees; in still other embodiments, the angle may be approximately 45 degrees. Certain embodiments may comprise an actuator rod between the actuator and the implant, wherein the actuator rod comprises a flexible end proximal to the implant.

Other embodiments of the present disclosure comprise a method for approximation of soft tissues, the method comprising. The method may comprise: providing an implant system comprising an elongate arm having a first end and a second end; a cartridge assembly proximal to the first end, wherein the cartridge assembly comprises a plurality of implants; and an actuator configured to discharge an implant from the cartridge assembly. The method may also comprise inserting the elongate arm into a patient's nasal cavity and locating the first end proximal to a target implant location. The method may also comprise actuating the actuator; and discharging an implant into the target implant location.

Other embodiments of the present disclosure comprise an implant for use in approximating tissues, the implant comprising: a base portion; a stem; and a head portion configured for capturing tissue during use. In certain embodiments, the implant may comprise a base portion that is T-shaped or L-shaped. The head portion may be asymmetric and/or comprise a barb. In certain embodiments, the head portion comprises a pair of extensions extending past the stem and a slot in each extension. In certain embodiments, the implant is cannulated. The implant may comprise an aperture extending through the implant.

Certain embodiments of the present disclosure comprise an implant system comprising: a first elongate arm having a first end and a second end; an implant proximal to the first end; a handle assembly proximal to the second end, wherein the handle assembly comprises a handle and an actuator; a first actuator rod comprising a first flexible portion proximal to the first end, wherein the first flexible portion is configured to engage the implant; and a second actuator rod comprising a second flexible portion proximal to the first end, wherein the second flexible portion comprises a first tip configured to penetrate tissue In certain embodiments, upon partial actuation of the actuator: the actuator is operatively engaged with the first and second actuator rods; the first flexible portion of the first actuator rod is engaged with the implant; and the second actuator rod is configured such that the first tip extends past the implant.

In certain embodiments, upon full actuation of the actuator: the actuator is operatively engaged with the first and second actuator rods; the implant is discharged from the implant system; and the second actuator rod is configured such that the first tip extends past the implant. In certain embodiments, the implant comprises a bevel proximal to the a distal end of the implant. In specific embodiments, the bevel directs the implant toward the second flexible portion when the implant is penetrating into tissue during use.

In certain embodiments, the implant comprises an aperture and the second flexible portion is configured to extend through the aperture upon full actuation of the actuator. In specific embodiments, the implant comprises a slot and the second flexible portion is configured to extend through the slot upon full actuation of the actuator. In certain embodiments, the second flexible portion comprises a second tip. The second tip may be configured to extend through an aperture or slot in the implant.

Certain embodiments comprise a system configured to discharge the implant at an angle to the first elongate arm. In specific embodiments, the implant is part of a cartridge assembly when the actuator is actuated. Certain embodiments may further comprise a second elongate arm comprising a distal end and a proximal end. In specific embodiments, the second elongate arm is generally parallel to the first elongate arm when the actuator is not actuated.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF EXEMPLARY EMBODIMENTS

Figure 1:
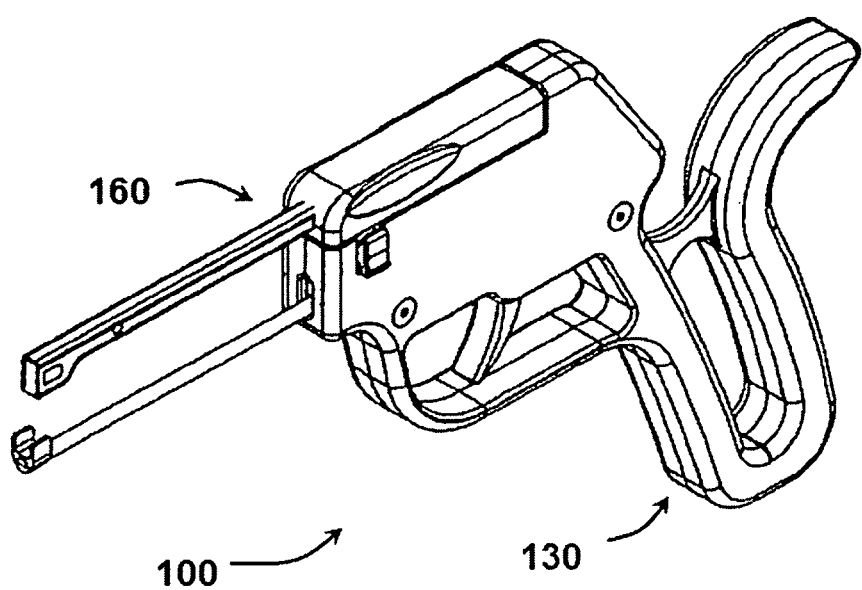
FIG. 1 illustrates a perspective view of an exemplary embodiment of an implant system.
Figure 2:
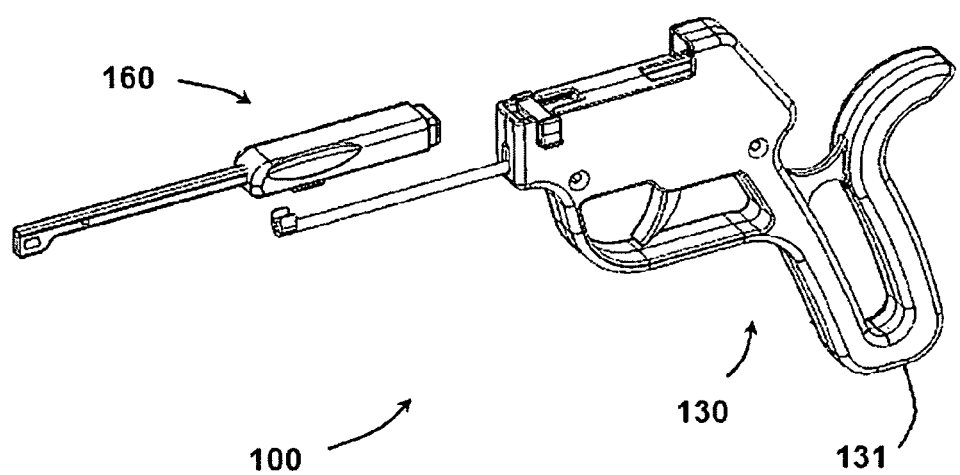
FIG. 2 illustrates a perspective view of the exemplary embodiment of FIG. 1.
Figure 3:
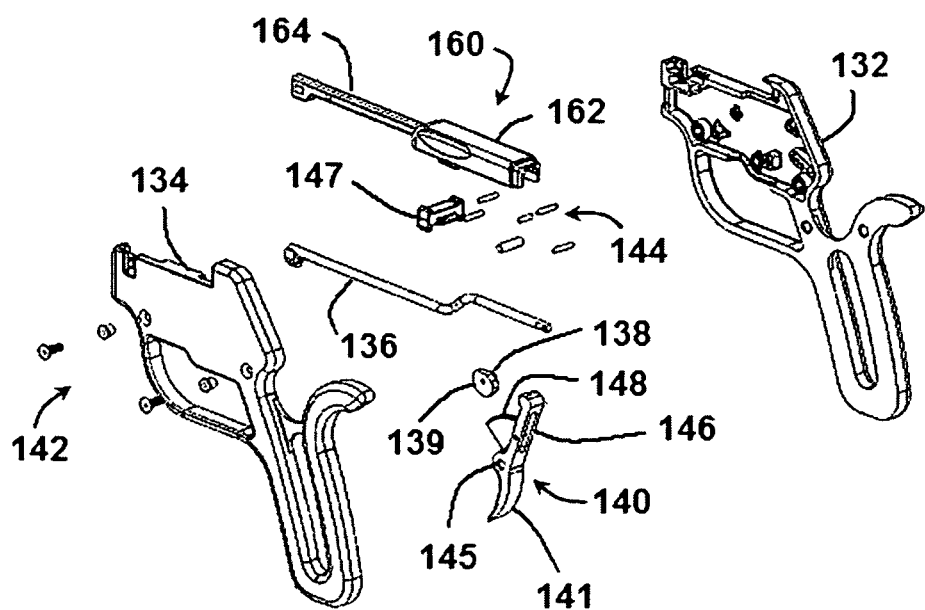
FIG. 3 illustrates an exploded view of the exemplary embodiment of FIG. 1.
Figure 4:
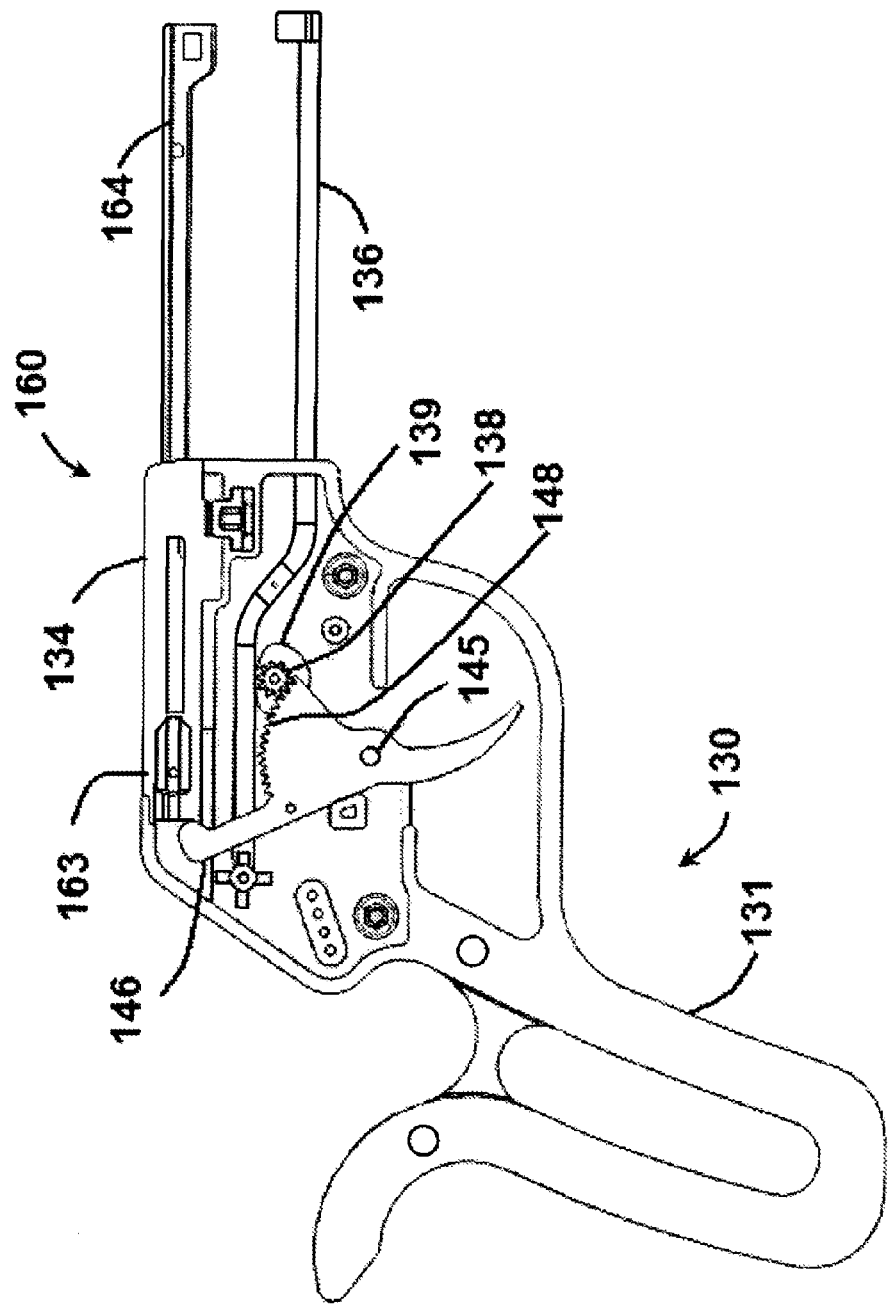
FIG. 4 illustrates a partial section side view of the exemplary embodiment of FIG. 1.
Figure 5:
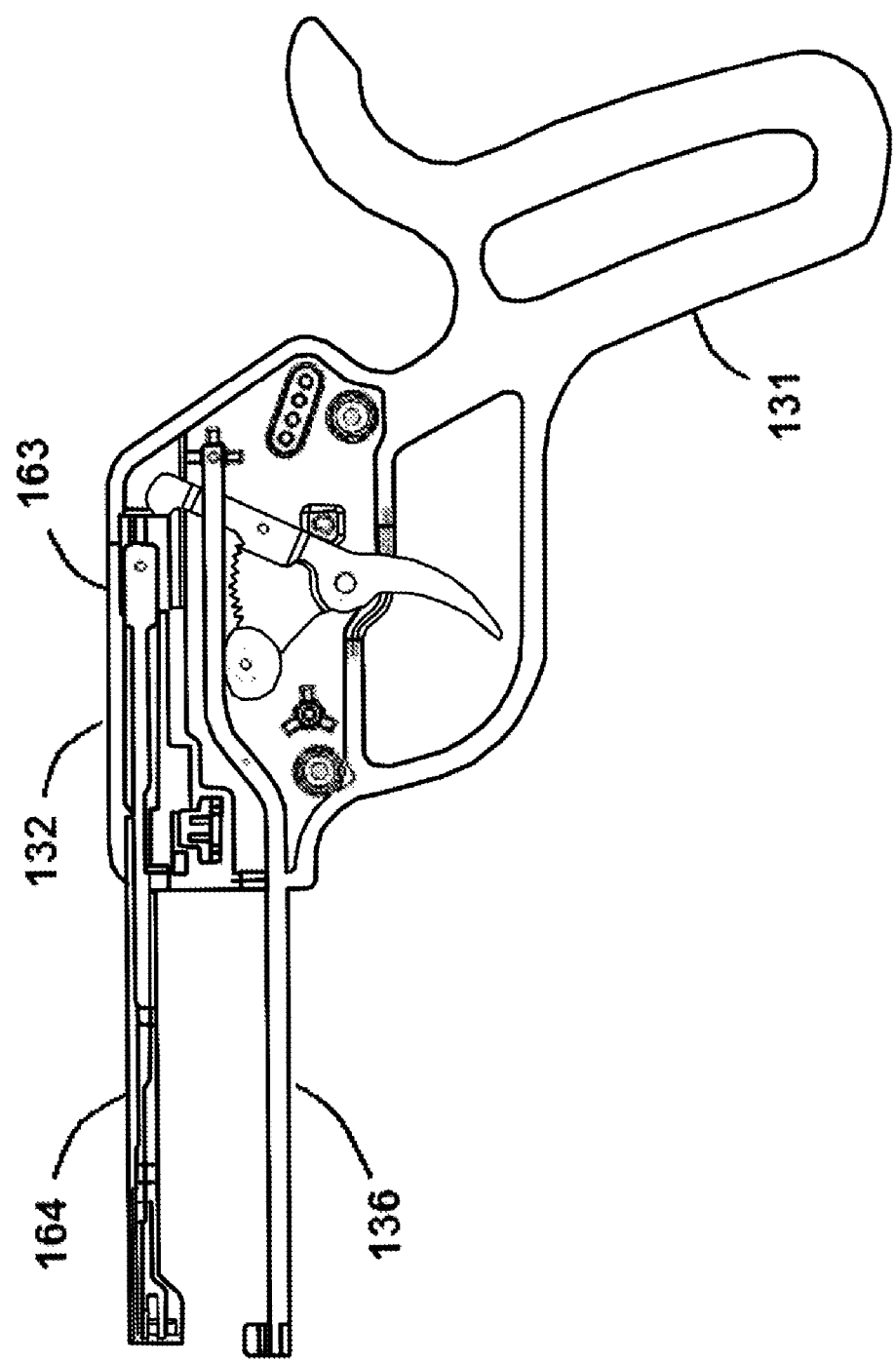
FIG. 5 illustrates a partial section side view of the exemplary embodiment of FIG. 1.
Figure 6:
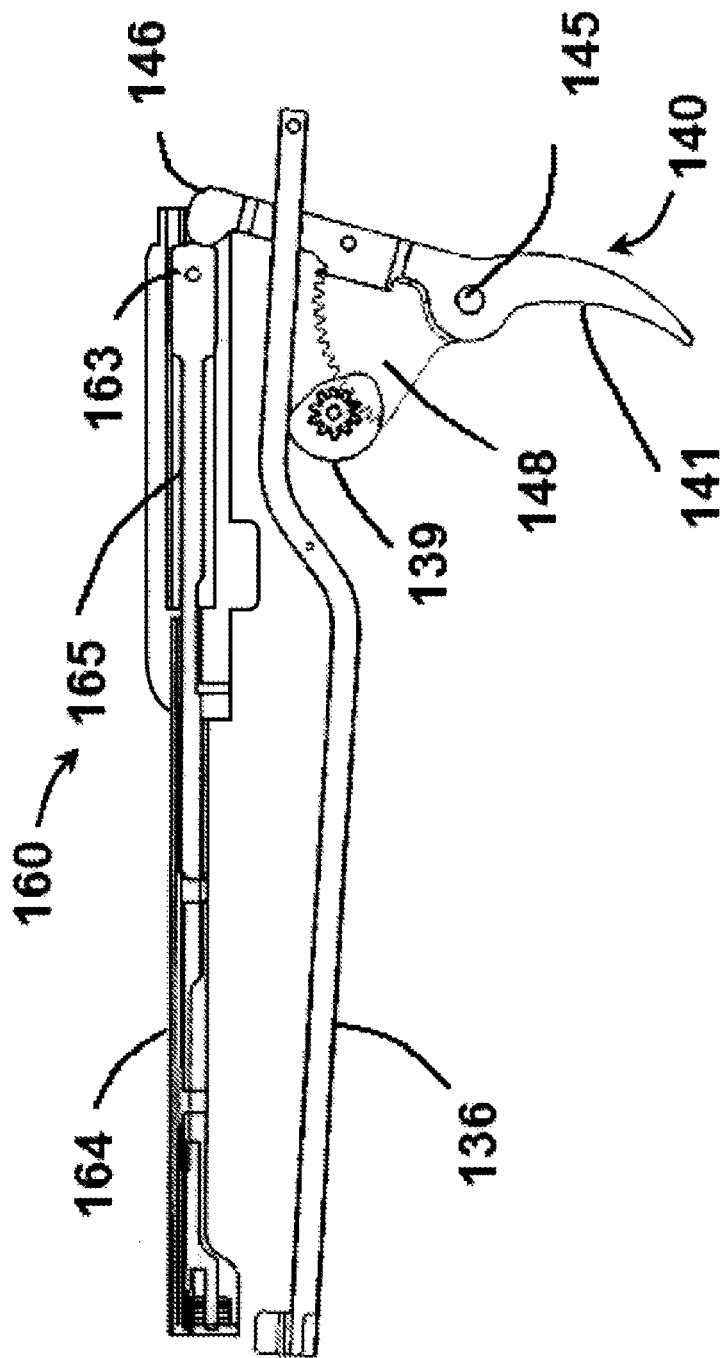
FIG. 6 illustrates a partial side view of the exemplary embodiment of FIG. 1.

Referring now to the exemplary embodiment shown in FIGS. 1 through 12, an implant system 100 comprises a handle assembly 130 and a cartridge assembly 160 that can be coupled to or separated from handle assembly 130. Handle assembly 130 comprises a right casing 132 and a left casing 134, a counter tension arm 136, a cam gear 138, a handle 131, and an actuator 140. In the embodiment shown, actuator 140 comprises a trigger 141 and an actuator arm 146. In other embodiments, actuator 140 may comprise different configurations, such as including a cam surface, a lever, switch, or other actuating mechanism. In the exemplary embodiment shown, actuator 140 also comprises a pivot point 145 and a gear 148, Handle assembly 130 further comprises a plurality of screws 142 and pins 144 to couple right casing 132 to left casing 134. Right casing 132 and left casing 134 can be coupled with glue, ultrasonic welding or other commonly practiced methods. Cartridge assembly 160 comprises a housing 162 and a cartridge arm 164. A cartridge lock 147 can be positioned to retain cartridge assembly 160 to handle assembly 130 or to release cartridge assembly 160 from handle assembly 130.

Figure 7:
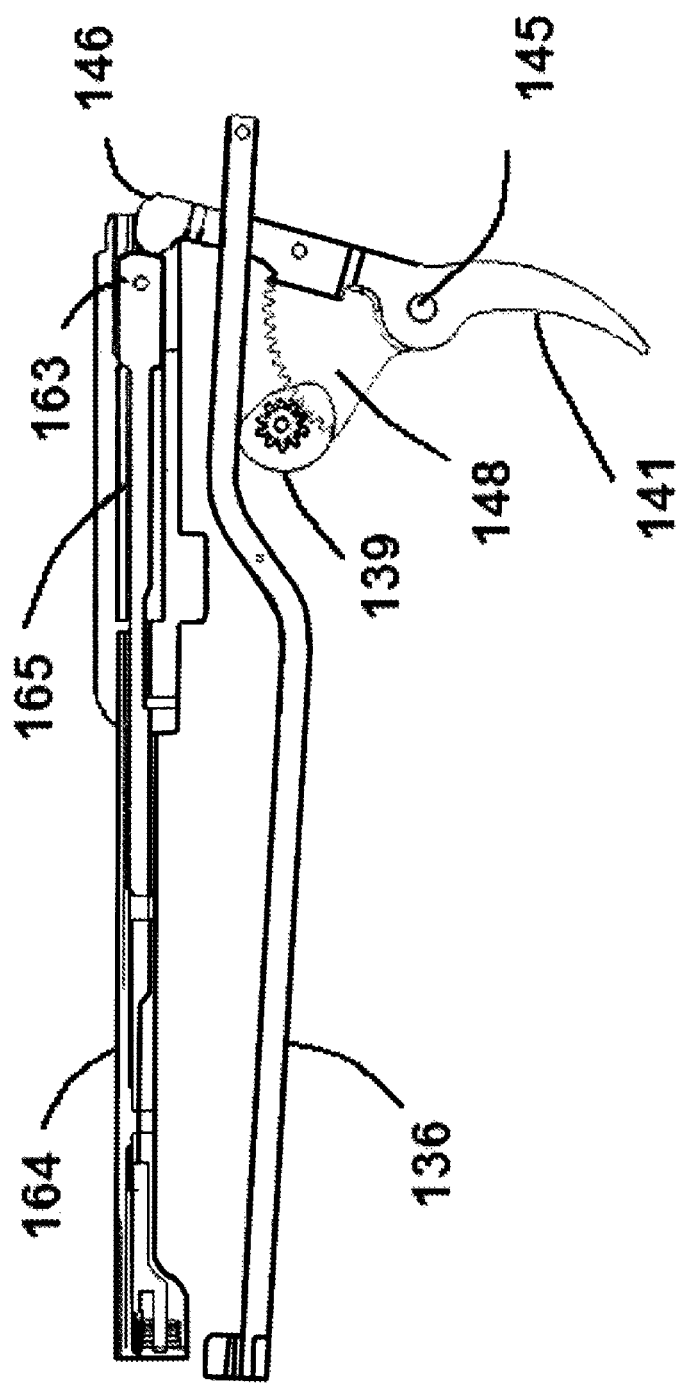
FIG. 7 illustrates a partial side view of the exemplary embodiment of FIG. 1.
Figure 8:
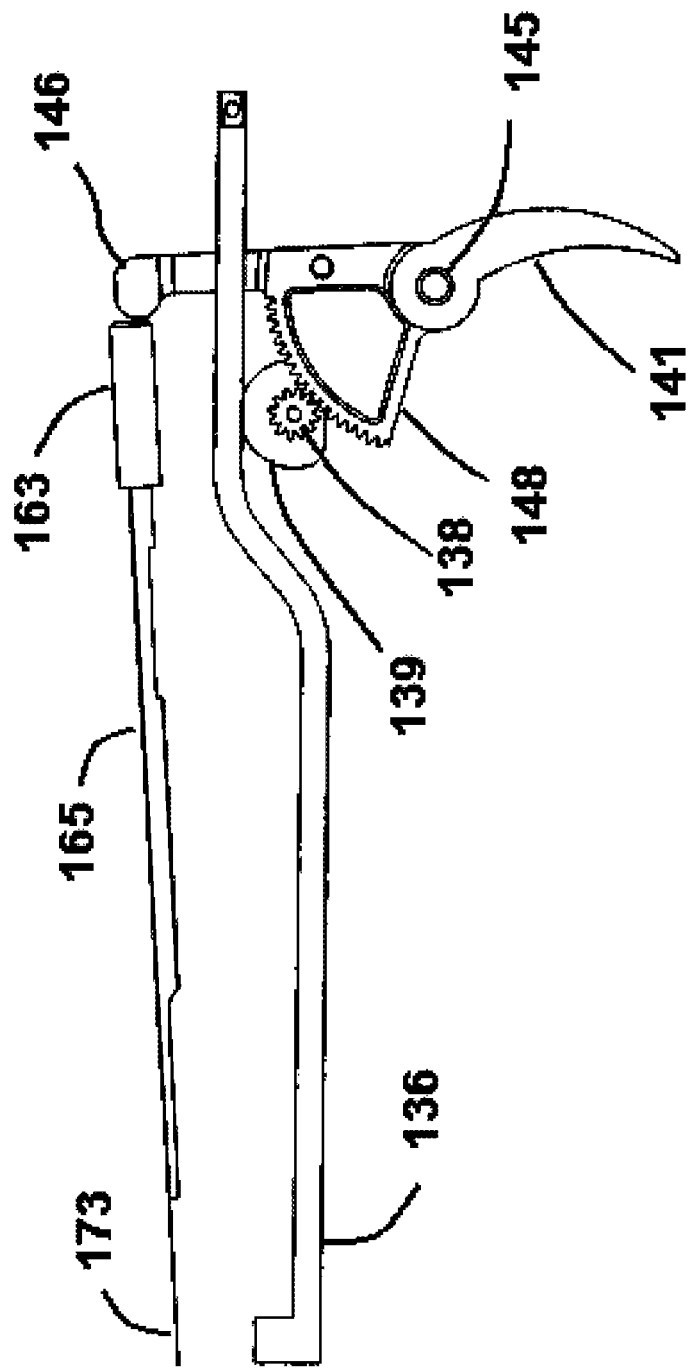
FIG. 8 illustrates a partial side view of the exemplary embodiment of FIG. 1.

As shown in the views of FIGS. 4-8, cartridge assembly 160 comprises an actuator rod 165 with a ram 163. As actuator 140 is actuated (i.e. pulled toward handle 131), actuator 140 pivots around pivot point 145, and gear 148 engages cam gear 138. In addition, actuator arm 146 moves toward ram 163. As shown in FIG. 7, when actuator 140 is pulled a sufficient amount, actuator arm 146 engages ram 163 and moves actuator rod 165 within cartridge arm 164 of cartridge assembly 160.

In the exemplary embodiment shown in FIGS. 4-8, cam gear 138 has an eccentric cam surface 139 that engages counter tension arm 136. Eccentric cam surface 139 has an effective diameter that is variable for a portion of cam surface 139 and constant for a portion of cam surface 139. In this exemplary embodiment, the effective diameter is the distance from the center of cam gear 138 to the portion of cam surface 139 engaging counter tension arm 136. As cam gear 138 rotates (while actuator 140 is being pulled), cam surface 139 initially causes counter tension arm 136 to move towards cartridge arm 164. At a certain point in the actuation of actuator 140 (just past the location shown in FIG. 7), the effective diameter of cam surface 139 reaches a maximum value. As the actuation of actuator 140 is continued, counter tension arm 136 is moved to the position shown in FIG. 8. In this manner, counter tension arm 136 moves toward cartridge arm 164, and can provide backing support for tissue located between counter tension arm and cartridge arm 164.

Figure 9:
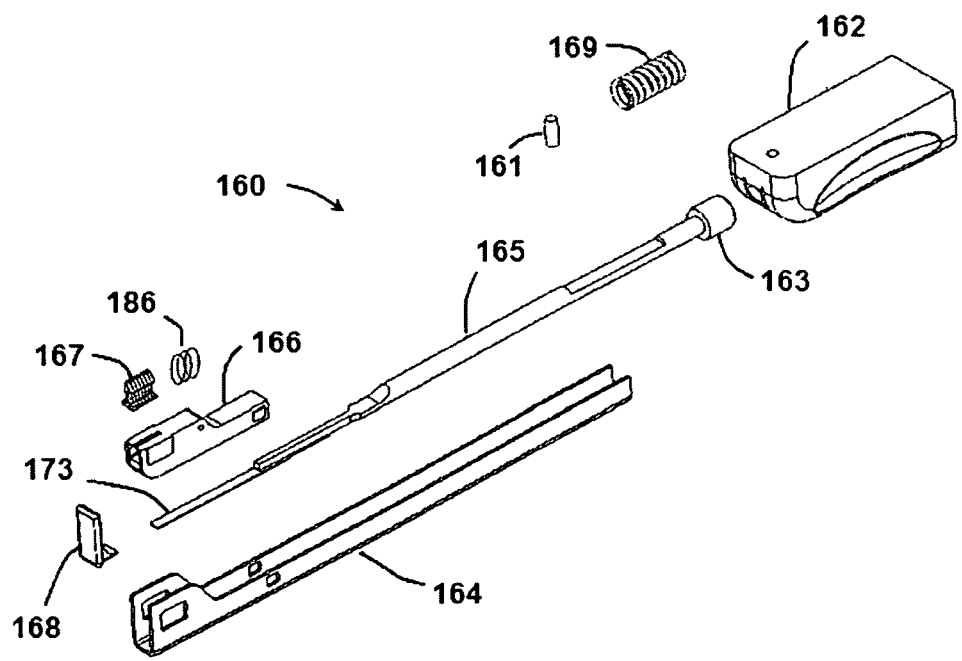
FIG. 9 illustrates a partial exploded view of the exemplary embodiment of FIG. 1.
Figure 10:
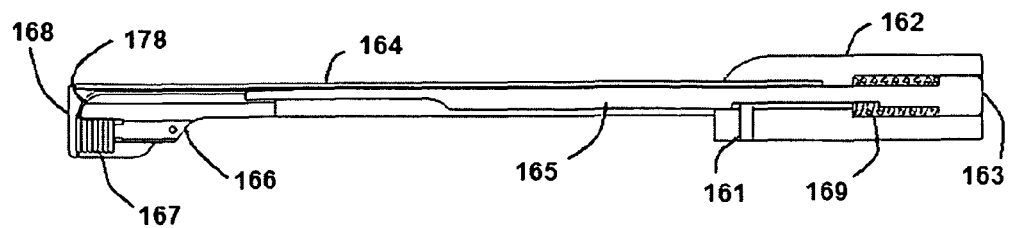
FIG. 10 illustrates a partial section view of the exemplary embodiment of FIG. 1.

In addition to the movement of counter tension arm 136, the actuation of actuator 140 also causes actuator arm 146 to move towards ram 163. As explained above, when actuator arm 146 reaches the position shown in FIG. 7, it engages ram 163 and causes actuator rod 165 to slide within cartridge assembly 160. As shown in FIGS. 9 and 10, cartridge assembly 160 comprises housing 162, cartridge arm 164, ram 163, actuator rod 165, a cartridge 166 holding a plurality of implants 167, a guide 168, a support member 161 and a biasing member 169. Actuator rod 165 comprises a distal end 173 that engages guide 168 during operation. Biasing member 169 exerts a force against ram 163 and biases ram 163 and actuator rod 165 towards the proximal end of cartridge assembly 160 (i.e. the end distal from guide 168). As previously described, actuator 140 can be actuated so that actuator arm 146 contacts ram 163. Continued actuation of actuator 140 can cause actuator arm 146 to overcome the force exerted by biasing member 169, so that ram 163 and actuator rod 165 are moved towards guide 168.

Figure 11:
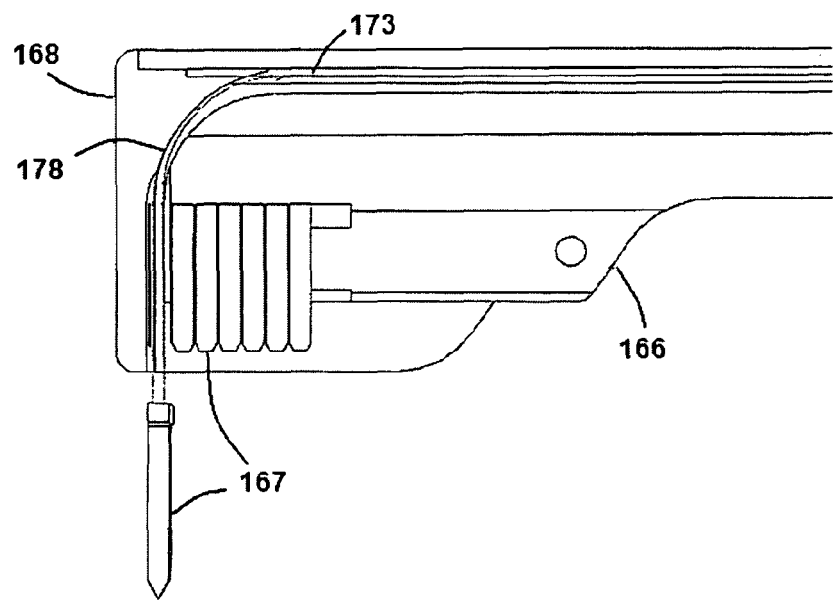
FIG. 11 illustrates a partial section view of the exemplary embodiment of FIG. 1.

In the exemplary embodiment shown, guide 168 comprises a curved surface 178 that receives distal end 173 as actuator rod 165 is actuated during operation. As actuator rod 165 moves toward guide 168, distal end 173 engages curved surface 178 and is directed towards an implant 167. Distal end 173 can thereby displace an implant 167 from cartridge 166 (as shown in FIG. 11). During use, cartridge 166 can be located proximal to a tissue (not shown) into which implant 167 will be implanted. Distal end 173 can exert a sufficient force on implant 167 to cause implant 167 to penetrate the tissue. Though the guide 168 is shown to translate the distal end 173 ninety degrees, it should be noted that this translation can be any direction between 0° and 180°. In the exemplary embodiment shown, implant 167 is therefore ejected or discharged at an angle of approximately ninety degrees to cartridge arm 164. In other embodiments, implant 167 may be discharged at an angle to cartridge arm 164 that is greater than or less than ninety degrees. In one exemplary embodiment, implant 167 may be discharged at an angle to cartridge arm 164 that is approximately 45 degrees.

Figure 12:
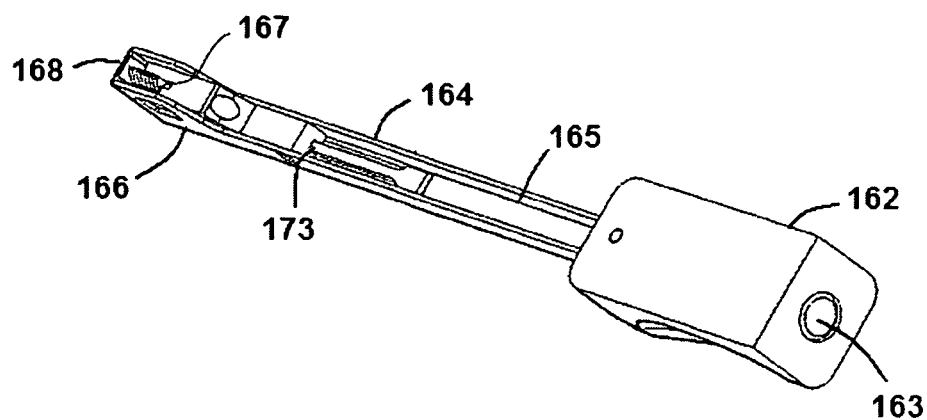
FIG. 12 illustrates a perspective view of a component of the exemplary embodiment of FIG. 1.

Referring now to the exemplary embodiment of FIG. 12, a perspective view of the underneath side of cartridge assembly 160 shows one orientation of housing 162, cartridge arm 164, actuator rod 165, cartridge 166, implants 167 and guide 168. In the exemplary embodiment shown, distal end 173 is narrower than the remaining portions of actuator rod 165 and enters cartridge 166. In other exemplary embodiments, distal end 173 may have a different configuration than that shown in FIG. 12. For example distal end 173 may not be narrower than the remaining portions of actuator rod 165. Implants 167 extend from cartridge 166 in a manner so that distal end 173 can discharge the implant 167 that is proximal to guide 168. In certain embodiments, a biasing member 186 biases implants 167 towards guide 168. When one implant 167 is discharged, distal end 173 is retracted back into the cartridge assembly 160, and the remaining implants 167 move towards guide 168. A subsequent actuation of actuator 140 will then discharge an additional implant 167.

Figure 13:
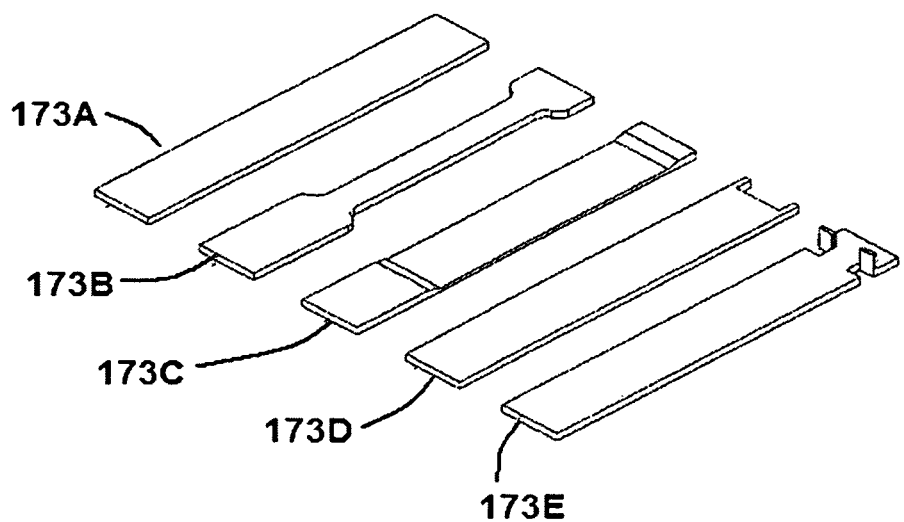
FIG. 13 illustrates a perspective view of a component of the exemplary embodiment of FIG. 1.

As shown in FIG. 13, distal end 173 may comprise any of several different configurations. For example, distal end 173 may be a ribbon or strip of constant width as shown in end 173A, or distal end 173 may comprise a varying width as shown in end 173B. Distal end 173 may also comprise a varying thickness as shown in an end 173C. Distal end 173 may also have a cut-out (or cut-outs) as shown in 173D or tabs as shown in 173E. Distal end 173 may be made of any suitable material. Examples of such materials comprise plastic and/or metal, including superelastic materials such as nickel titanium, commonly referred to as Nitinol®. It is understood by one skilled in the art that other embodiments of distal end 173 may comprise combinations of the features disclosed, or additional features.

Figure 14:
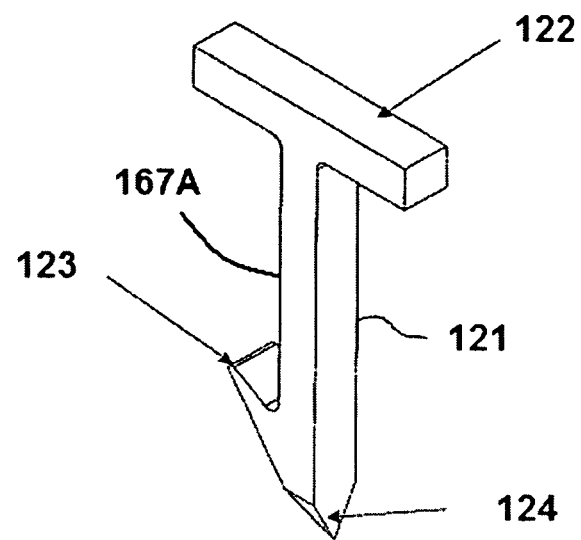
FIGS. 14-25 illustrate perspective and orthogonal views of a component of the exemplary embodiment of FIG. 1.
Figures 15, 16:
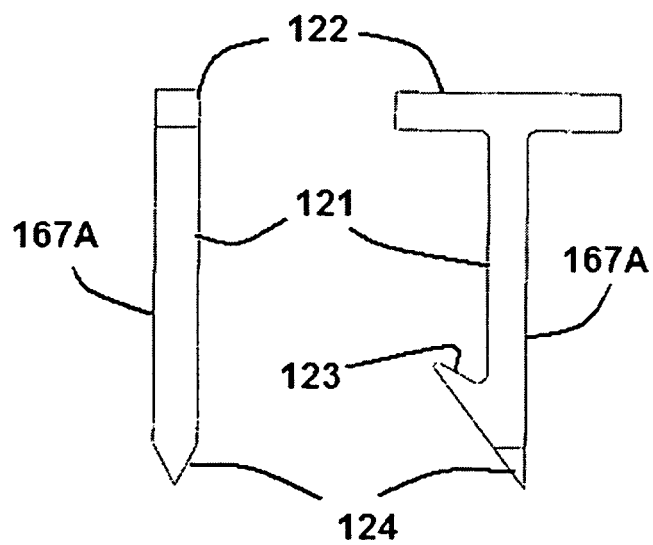
Figure 17:
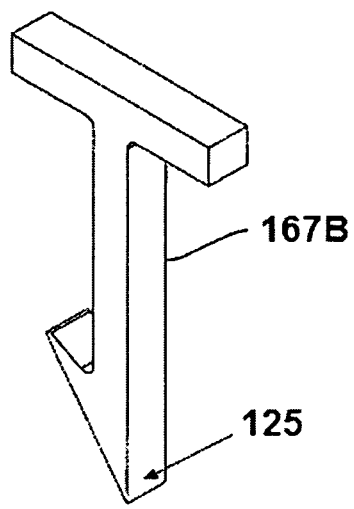
Figure 18:
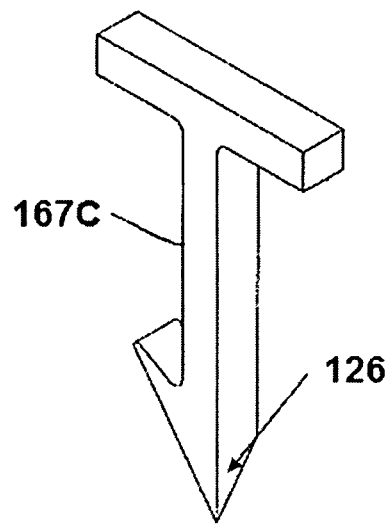
Figure 19:
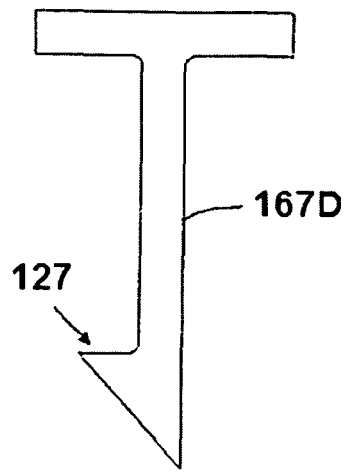
Figure 20:
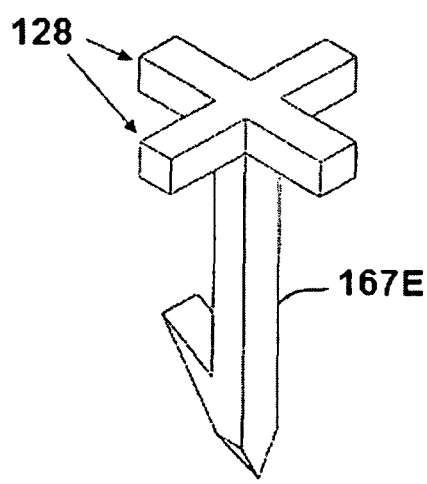
Figure 21:
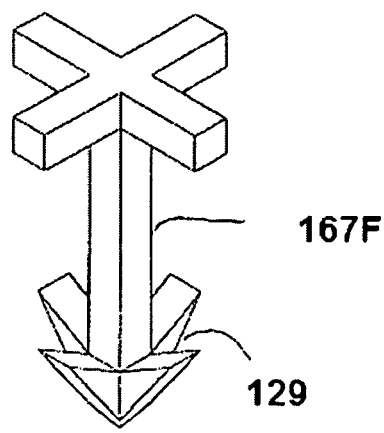
Figure 22:
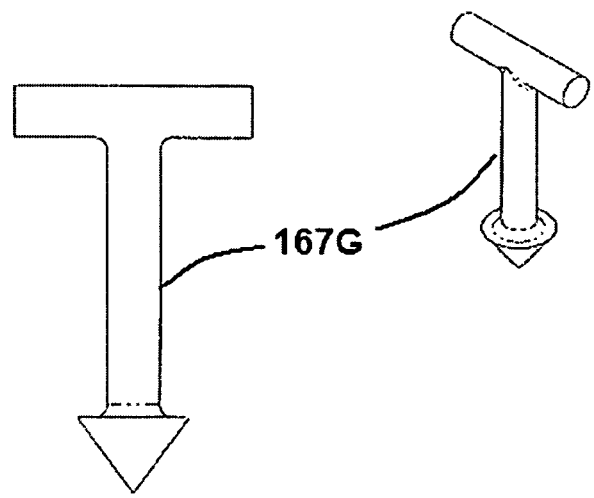
Figure 23:
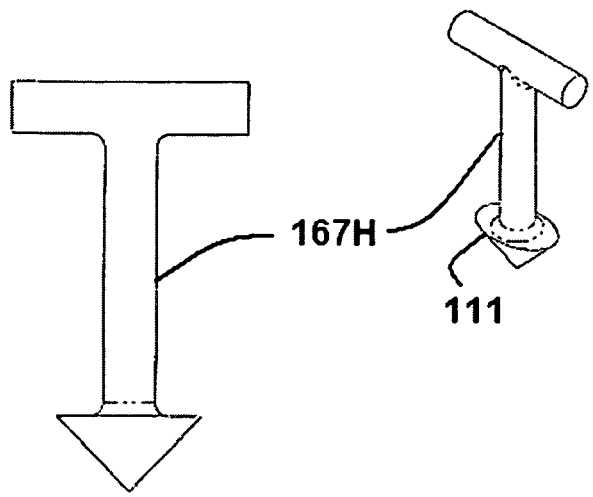
Figure 24:
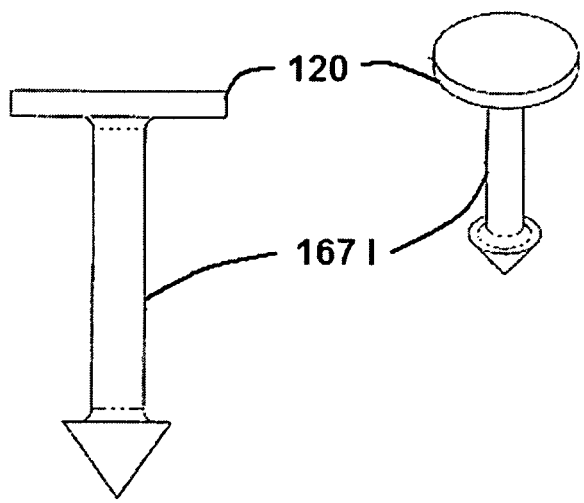
Figure 25:
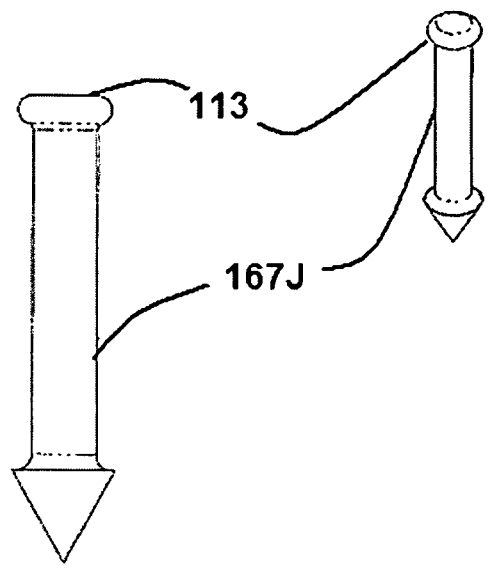

Referring now to FIGS. 14-25, various exemplary embodiments of implants are illustrated. As shown in FIGS. 14-16, implant 167A comprises a post 121, a transverse section 122, a barb 123, and a pointed tip 124. Pointed tip 124 reduces the amount of force needed to insert implant 167A into tissue (not shown), and barb 123 assists in holding implant 167A in the desired location. Transverse section 122 holds the tissue in place and also reduces the likelihood that implant 167A will be accidentally pushed through the tissue into which it is inserted. Implant 167B shown in FIG. 17 is similar to implant 167A, but comprises a tip 125 with a straight edge rather than a point. Implant 167C is also similar, but comprises a tip 126 with a single beveled point rather than the multiple bevel point shown in FIG. 14. Implant 167D shown in FIG. 19 comprises a barb 127 that is perpendicular to the primary axis (not shown) of the implant. Implant 167E of FIG. 20 comprises multiple transverse sections 128, while implant 167F shown in FIG. 21 also comprises multiple barbs 129. FIG. 22 shows implant 167G with a round cross-section instead of the rectangular or square cross-section shown in previous embodiments. FIG. 23 shows an implant with an elliptical barb 111. FIG. 24 illustrates an implant 167I with a disc-shaped transverse member 112, while FIG. 25 illustrates an implant 167J with a rib 113 rather than a transverse member.

In certain embodiments implant 167 may be approximately four to six millimeters long, two to three millimeters wide, and approximately 0.4 to 0.7 millimeters thick. More specifically, implant 167 may be 4.5 to 5.5 millimeters long, 2.3 to 2.7 millimeters wide, and 0.5 to 0.6 millimeters thick. In a specific exemplary embodiment, implant 167 is approximately 5 millimeters long, 2.5 millimeters wide, and 0.55 millimeters thick. In certain exemplary embodiments, implant 167 comprises an absorbable copolymer comprising approximately 60 to 80 percent polyactide and approximately 20 to 40 percent polyglycolide. More specifically, implant 167 may comprise an absorbable copolymer comprising approximately 65 to 75 percent polyactide and approximately 25 to 35 percent polyglycolide. In a specific exemplary embodiment, implant 67 comprises an absorbable copolymer comprising approximately 70 percent polyactide and approximately 30 percent polyglycolide. In still other specific embodiments, implant 67 comprises an absorbable copolymer comprising approximately 90 percent polyactide and approximately 10 percent polyglycolide. In other embodiments, implants 167 may be non-absorbable.

Figure 26:
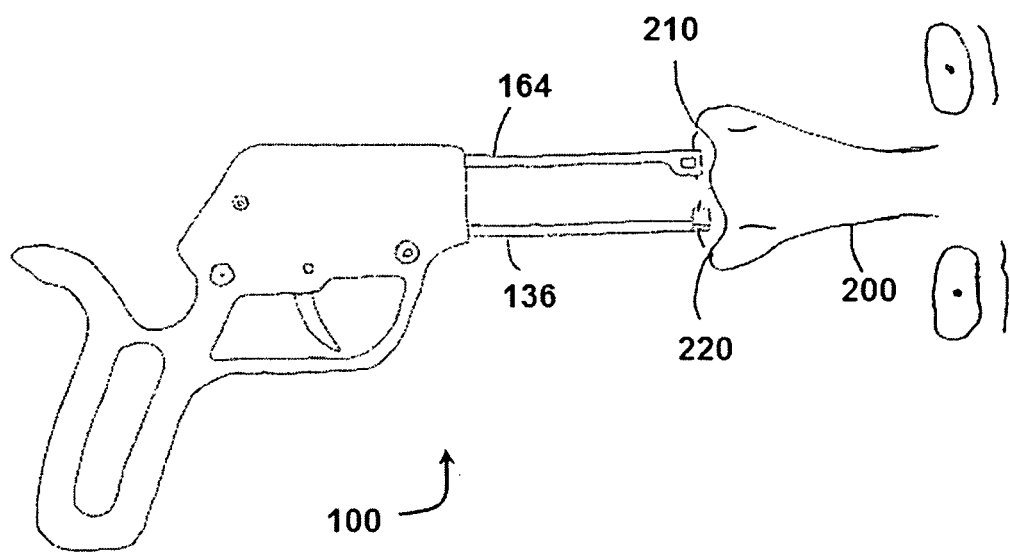
FIGS. 26-27 illustrate the exemplary embodiment of FIG. 1 during use.
Figure 27:
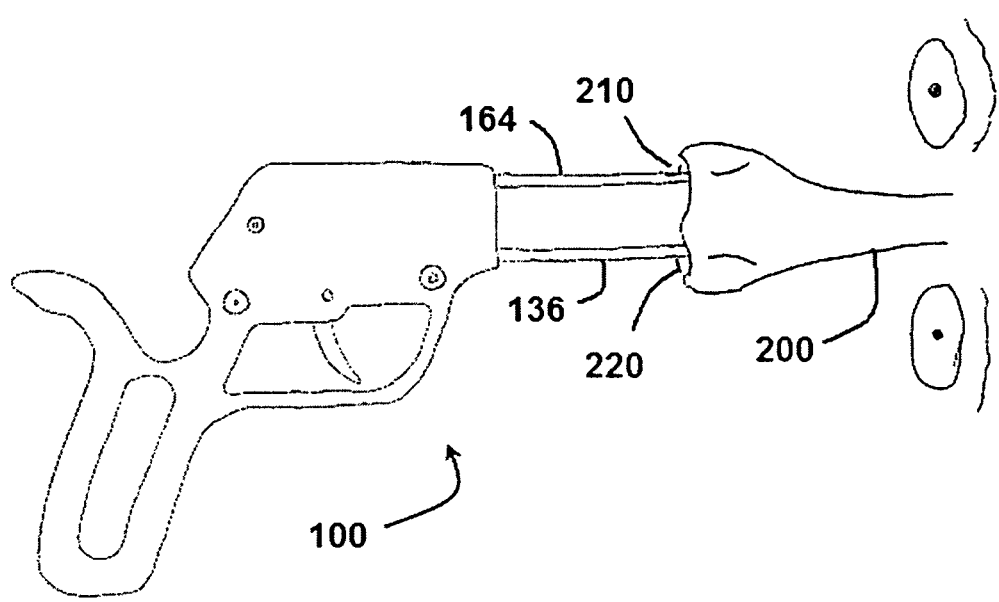

Referring now to FIGS. 26 and 27, implant system 100 is shown in an exemplary method of use during a nasal septum reconstruction. As shown in FIG. 26, implant system 100 is positioned proximal to a patient's nose 200. In this embodiment, implant system 100 is positioned so that cartridge arm 164 is proximal to a nasal cavity 210 and counter tension arm 136 is proximal to a nasal cavity 220.

Referring now to FIG. 27, implant system 100 is then positioned so that cartridge arm 164 is inserted into nasal cavity 210 and counter tension arm 136 is inserted into nasal cavity 220. Implant system 100 is inserted the desired amount so that the distal ends of cartridge arm 164 and counter tension arm 136 are located proximal to a target location where it is desired to place an implant 167 into a mucoperichondrial flap formed in the patient's septum (not visible in FIGS. 26 and 27). When implant system 100 is positioned at the desired location, an operator stabilizes implant system 100 and actuates (i.e. pulls back on) actuator 140. As described in the discussion of the preceding figures, the actuation of actuator 140 causes counter tension arm 136 to move towards cartridge arm 164. Counter tension arm 136 can therefore provide backing support to the tissue into which the implant 167 will be inserted. The actuation of actuator 140 also causes distal end 173 of actuator rod 165 to force an implant 167 from cartridge 166.

In the embodiment shown in FIGS. 26 and 27, counter tension arm 136 supports tissue on one side of the patient's septum, while an implant 167 is inserted into a mucoperichondrial flap on the opposite side of the patient's septum. In certain exemplary embodiments, initial implants 167 are placed anteriorly and superiorly within nasal cavity 210 as compared to subsequent implants 167. In certain embodiments, implants 167 are placed within approximately two centimeters of each other. In other embodiments, implants 167 are placed within approximately 1.5 centimeters of each other, and in still other embodiments, implants 167 are placed within approximately one centimeter of each other.

In certain embodiments, implants 167 may be placed in both nasal cavities 210 and 220, while in other embodiments implants 167 may be placed in either nasal cavity 210 or nasal cavity 220. After the operator has placed implants in the bilayered mucosal flaps, the operator may visualize both nasal cavity 210 and 220 to assure adequate approximation and sufficient penetration of all staples through the flaps. After the tissue is appropriately approximated and all flaps are secured, the operator may dispose of cartridge 166 and any remaining implants 167. However, the remaining components of implant system 100 may be sterilized reused for future procedures.

Figure 28:
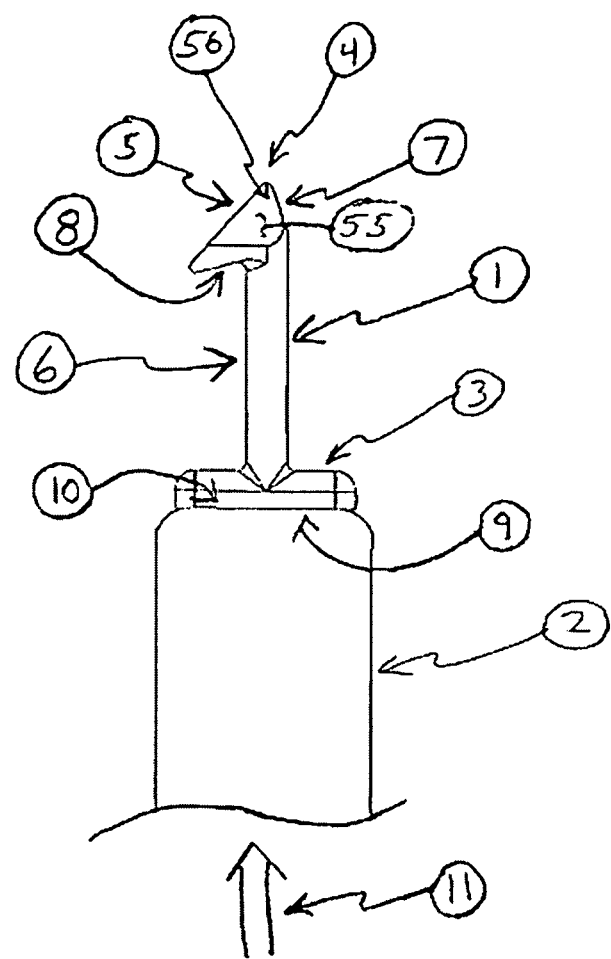
FIGS. 28-29 illustrate orthogonal views of a first exemplary embodiment of an implant and installation component.
Figure 29:
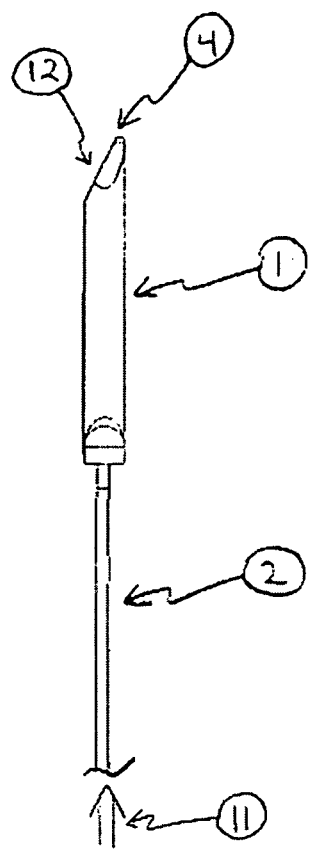

Referring now to FIGS. 28 and 29, front and side views are shown of one embodiment of an implant 1. Implant 1 can be configured for use in conjunction with previously-described embodiments. As shown, a base portion of implant 1 is engaged with a ribbon 2. In certain embodiments, ribbon 2 is equivalent to distal end 173 of actuator rod 165 of the embodiment described in FIGS. 1-12. In this embodiment, implant 1 comprises a T-shaped portion 3 which can act as a support against a tissue surface (not shown) when implant 1 is installed. In the embodiment shown, stem 6 couples T-shaped portion 3 to a barb 55 which has a point 4 created by the intersection of two faces 5 and 7. In exemplary embodiments, faces 5 and 7 do not need to be symmetrical or of the same length. As shown, the included angle 56 between faces 5 and 7 is slightly modified (as compared, for example, to embodiments shown in FIGS. 16 and 19) by configuring face 7 so that it is angled toward a center axis (not shown) of stem 6. By angling face 7 towards face 5, the intersection of faces 5 and 7 at point 4 is closer to the center axis of stem 6, which can provide for more stable tissue piercing during use. Certain embodiments may also comprise a face 12 as shown in FIG. 29 to further assist in piercing tissue during use. As shown in FIG. 28, a capture surface 8 provides an area that can assist in keeping the back side of pierced tissue in approximation with T-shaped portion 3. In the embodiment shown, capture surface 8 is extends from only on one side of the stem 6, but in other embodiments, it could also extend beyond both sides of stem 6.

During use, the embodiment shown in FIGS. 28 and 29 can be installed similar to other previously-described embodiments. For example, ribbon 2 can be pushed in the direction shown arrow 11. Ribbon 2 comprises a top portion 9 that can be pushed against the a bottom portion 10 of implant 1. The action of ribbon 2 against bottom portion 10 of implant 1 can assist pushing point 4 and barb 55 of implant 1 through the desired tissue(s). The tissue can then be captured between the T-shaped portion 3 and the capture surface 8. Implant 1 and ribbon 2, as with other embodiments presented in this document, can be made of metal or plastic, and in particular embodiments, biodegradable plastic. The ribbon 2, as with other embodiments presented in this document, can be made of metal or plastic and super-elastic materials such as nickel titanium, commonly referred to as Nitinol®.

Figure 30:
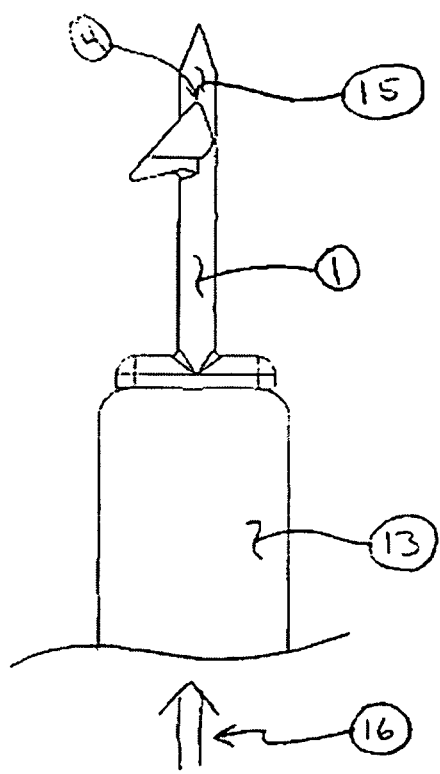
FIGS. 30-32 illustrate orthogonal views of a second exemplary embodiment of an implant and installation component.
Figure 31:
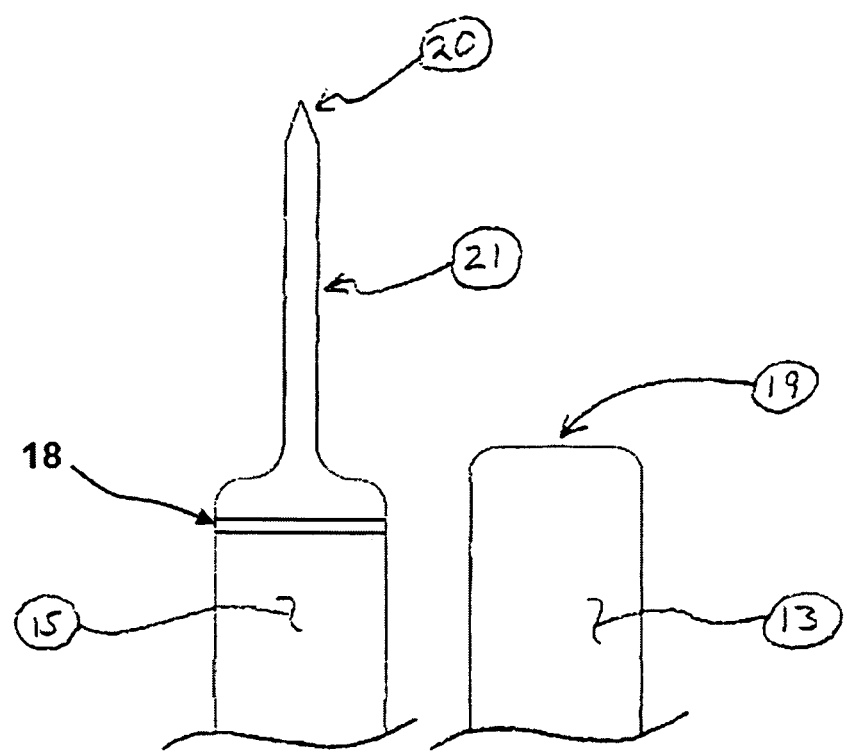
Figure 32:
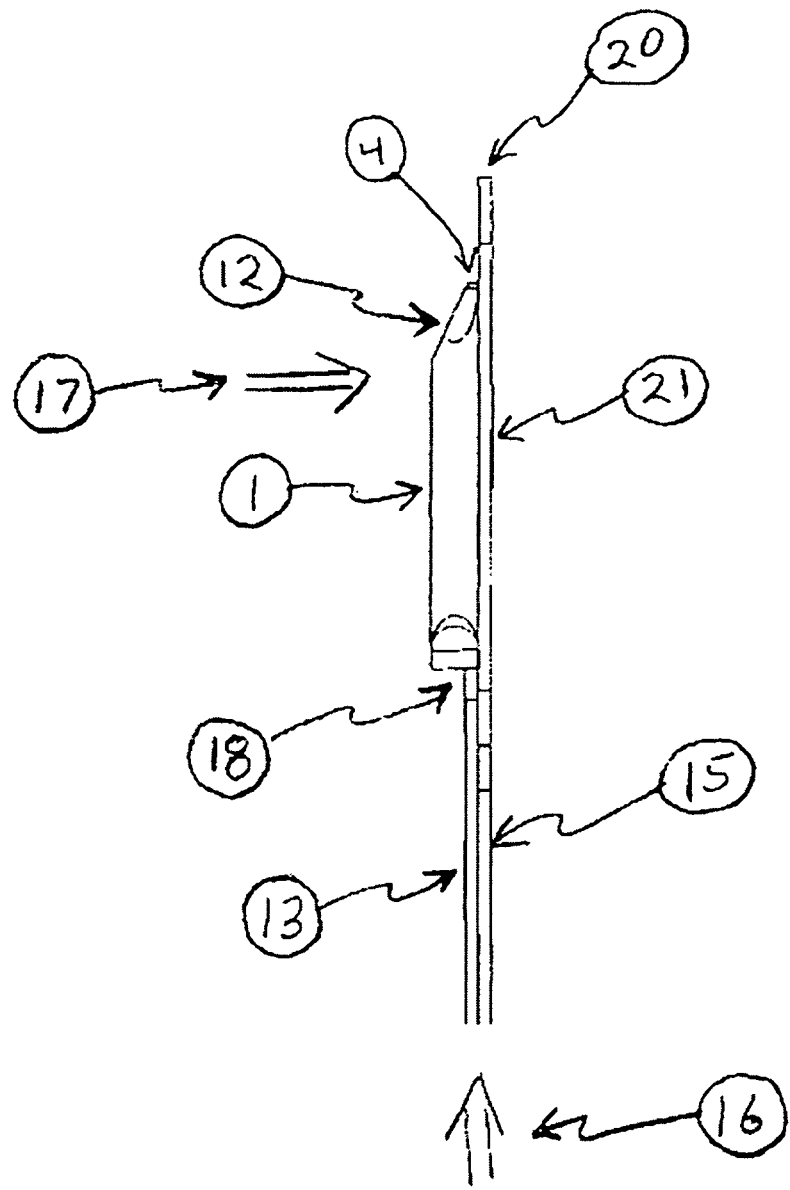

FIGS. 30-32 present an embodiment which comprises a second (or guide) ribbon 15 configured to create an initial hole in the tissue (not shown) and to give implant 1 stability during deployment. This system consists of the implant 1 being pushed from its bottom by a first ribbon 13. Second ribbon 15 has been placed against the first ribbon 13 and implant 1.

The two ribbons 13 and 15 can be seen more clearly in FIG. 31. The first ribbon 13 has a top surface 19 for pushing against the implant. The second ribbon 15 has a narrowed section or extension 21 with a point at the tip 20.

The action of this design can be best seen in FIG. 32. The first ribbon 13 pushes against the implant 1 at the base of T-shaped portion 18. In this exemplary embodiment, the tapered end or point 20 of the second ribbon 15 is shown above the implant tip 4 in order to create a leading hole in the tissue for easier deployment. In other embodiments, point 20 can be even with the implant tip 4 or slightly below. With extension 21 in place, the implant 1 is restricted from moving in that direction during installation. During installation, a tissue that implant 1 is being inserted through will exert reactionary forces on chamfer 12 as implant 1 passes through the tissue. These forces will to help direct implant 1 in a direction indicated by arrow 17 as implant 1 is pushed through the tissue. Such a configuration can create a more stable deployment of implant 1 by effectively holding implant 1 in place against extension 21.

Figure 33:
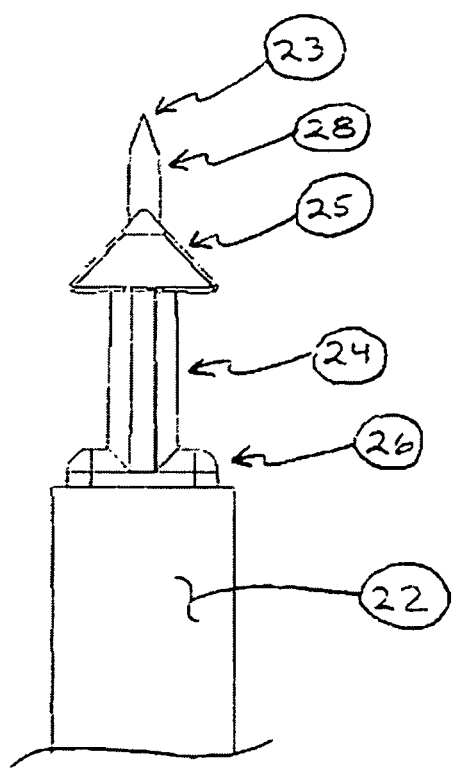
FIGS. 33-34 illustrate orthogonal and perspective views of a third exemplary embodiment of an implant and installation component.
Figure 34:
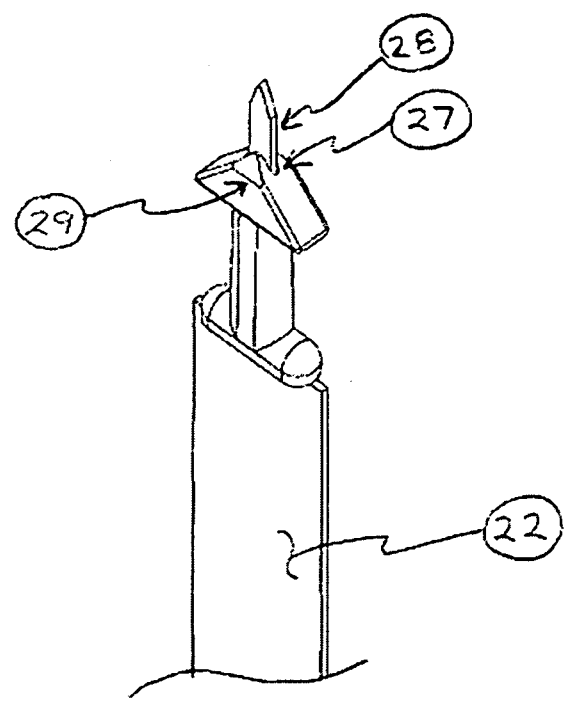

Another exemplary embodiment is shown in FIGS. 33 and 34. In this embodiment, however, implant 24 is hollow or cannulated and a ribbon 28 is placed in an aperture 27 extending through implant 24. In the embodiment shown, ribbon 28 has a leading point 23 and implant 24 has a T-shaped portion 26 and a tissue-capturing head 25. Extra bevels 29 can be added if desired to improve staple insertion through tissue. In alternate embodiments, a second ribbon can be used to push on a base portion of implant 24 during installation.

Figure 35:
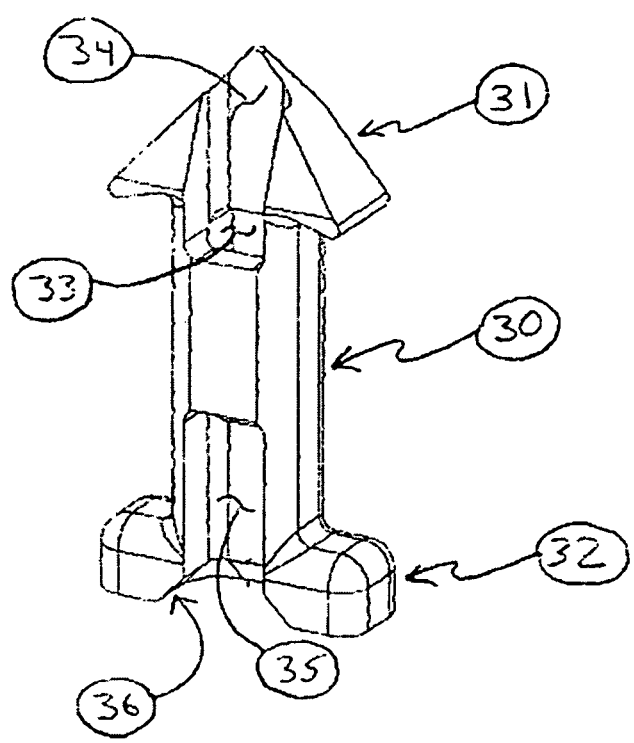
FIGS. 35-36 illustrate perspective views of a fourth exemplary embodiment of an implant.
Figure 36:
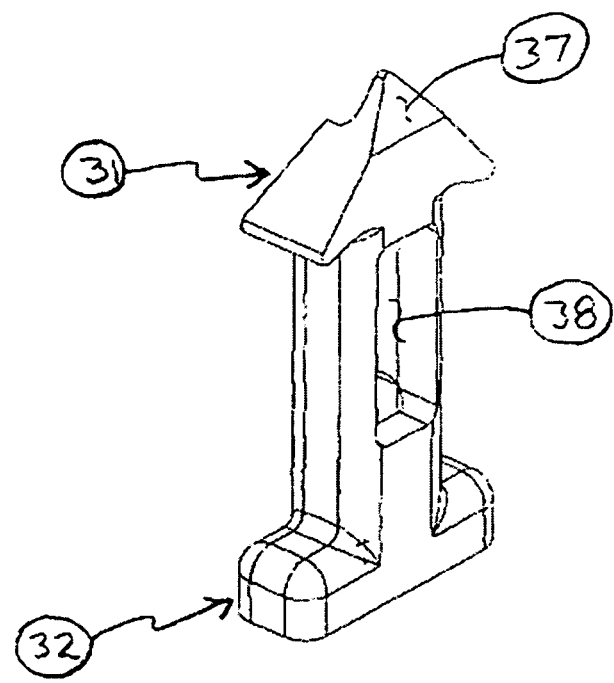

Yet another exemplary embodiment of a cannulated implant 30 is shown in FIGS. 35 and 36. In this embodiment, implant 30 comprises a stem, a head portion 31 with a chamfer 37, and a base with a T-shaped portion 32. The configuration of this embodiment can provide for a more simplified manufacturing process. For example, if implant 30 is made via an injection molding process, core pins of a mold (not shown) may be used create the cavities 34, 35, and 38 which can be coupled to create one passage 33. Passage 33 can be configured to accept a narrowed portion or extension of a ribbon, similar to aperture 27 in previously-described embodiments. A chamfer 36 may also be included to assist a ribbon extension in properly loading into the channel 33 in case the alignment is off slightly.

Figure 37:
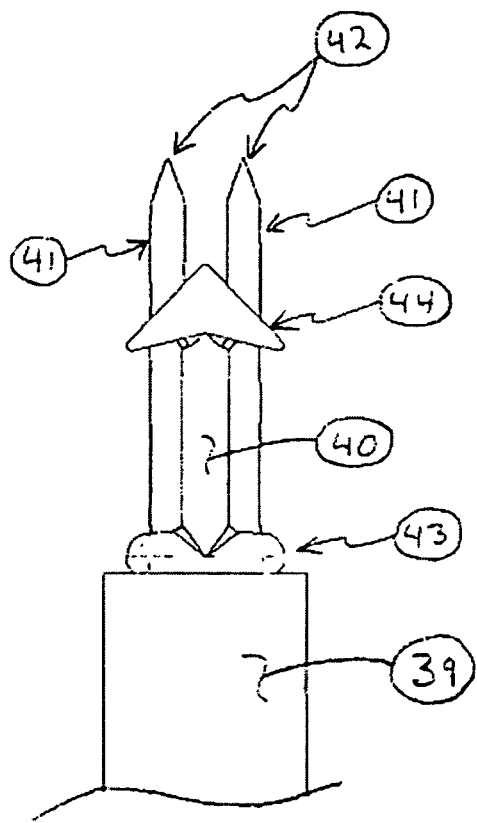
FIGS. 37-39 illustrate orthogonal and perspective views of a fifth exemplary embodiment of an implant and installation component.
Figure 38:
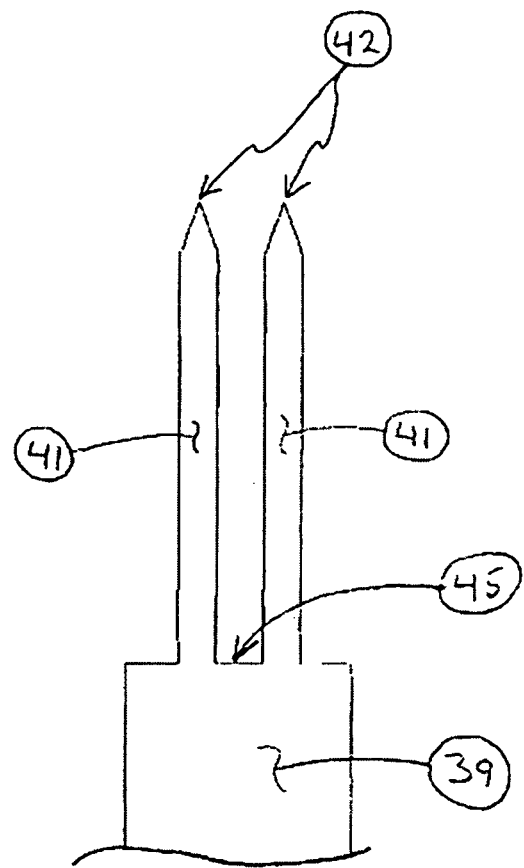
Figure 39:
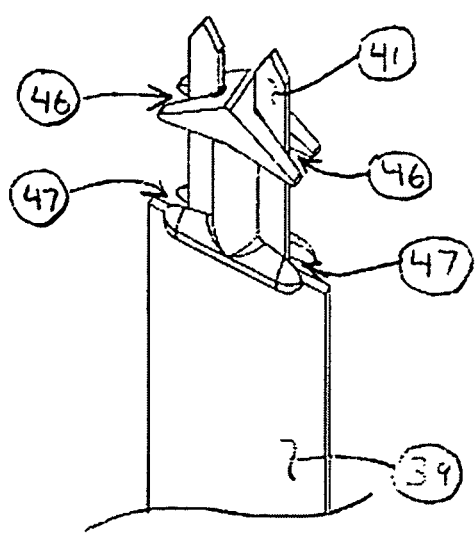

Another exemplary embodiment is shown in FIGS. 37, 38 and 39. In this embodiment, implant 40 comprises a stem, a head portion 44 and a base with a T-shaped portion 43. Instead of a single extension being placed in the middle of implant 40, two extensions 41 are used on either side of the center axis of implant 40. Extensions 41 may have leading points 42 and extend from a top portion 45 of a single ribbon 39. The embodiment shown may also provide simplify manufacturing processes (if, for example, implant 40 is manufactured by injection molding or machining) since the slots 46 and 47 are open to the sides.

Figure 40:
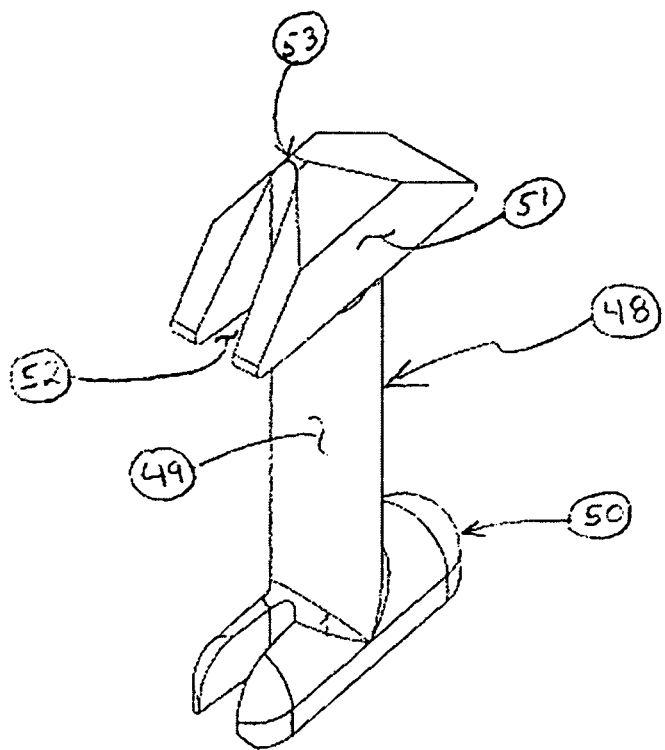
FIGS. 40-41 illustrate perspective and orthogonal views of a sixth exemplary embodiment of an implant.
Figure 41:
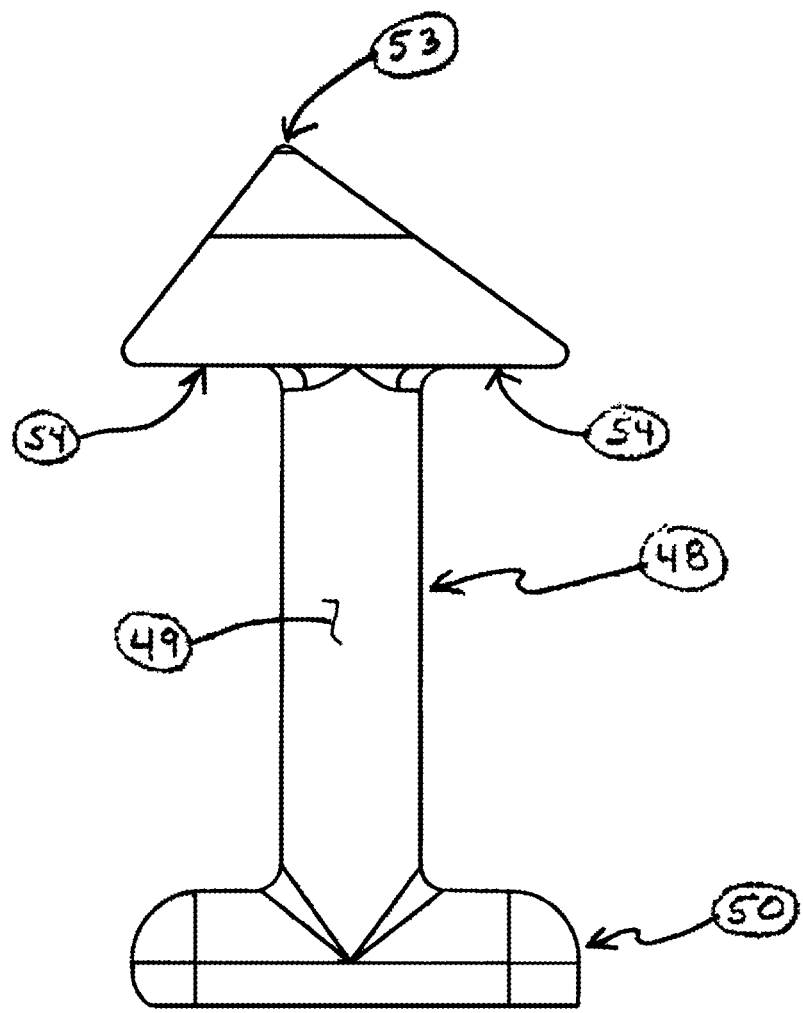

Still another exemplary embodiment is shown in FIGS. 40 and 41. In this embodiment, implant 48 comprises a stem 49, a head portion 51 and a base with a T-shaped portion 50. In the embodiment shown, head portion 51 comprises a pair of barbs 54 and an asymmetric point 53 that is closer to one barb 54 (i.e. the left barb 54 as shown in FIG. 41) than the other barb 54. The barb 54 that is closer to asymmetric point 53 also comprises a slot 52 that can accommodate a ribbon with a point (not shown) during deployment. In certain embodiments, asymmetric point 53 which can allow head portion 51 to blend with the ribbon more easily during deployment.

Figure 42A:
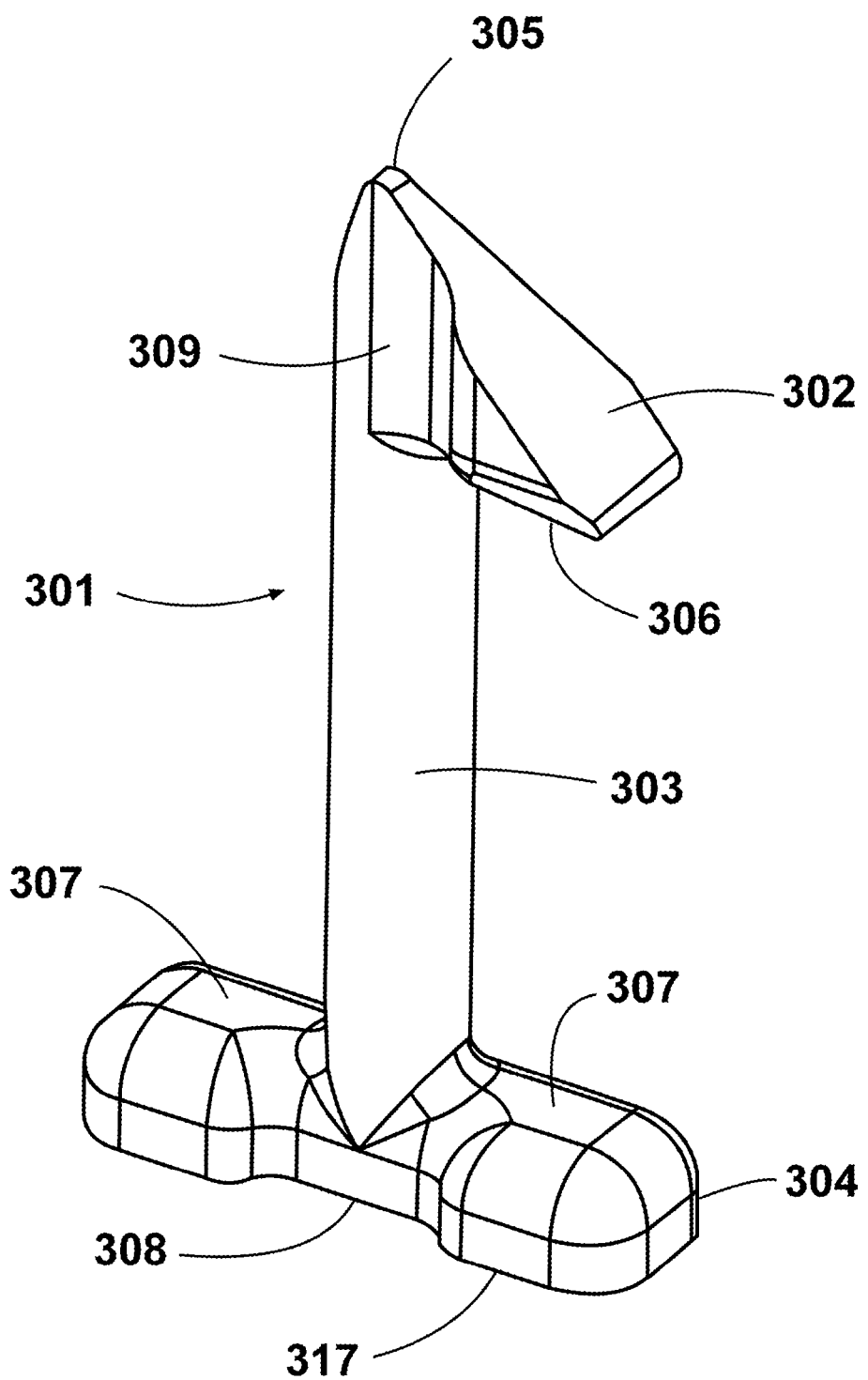
FIGS. 42A-46 illustrate orthogonal and perspective views of a fifth exemplary embodiment of an implant and installation component.
Figure 42B:
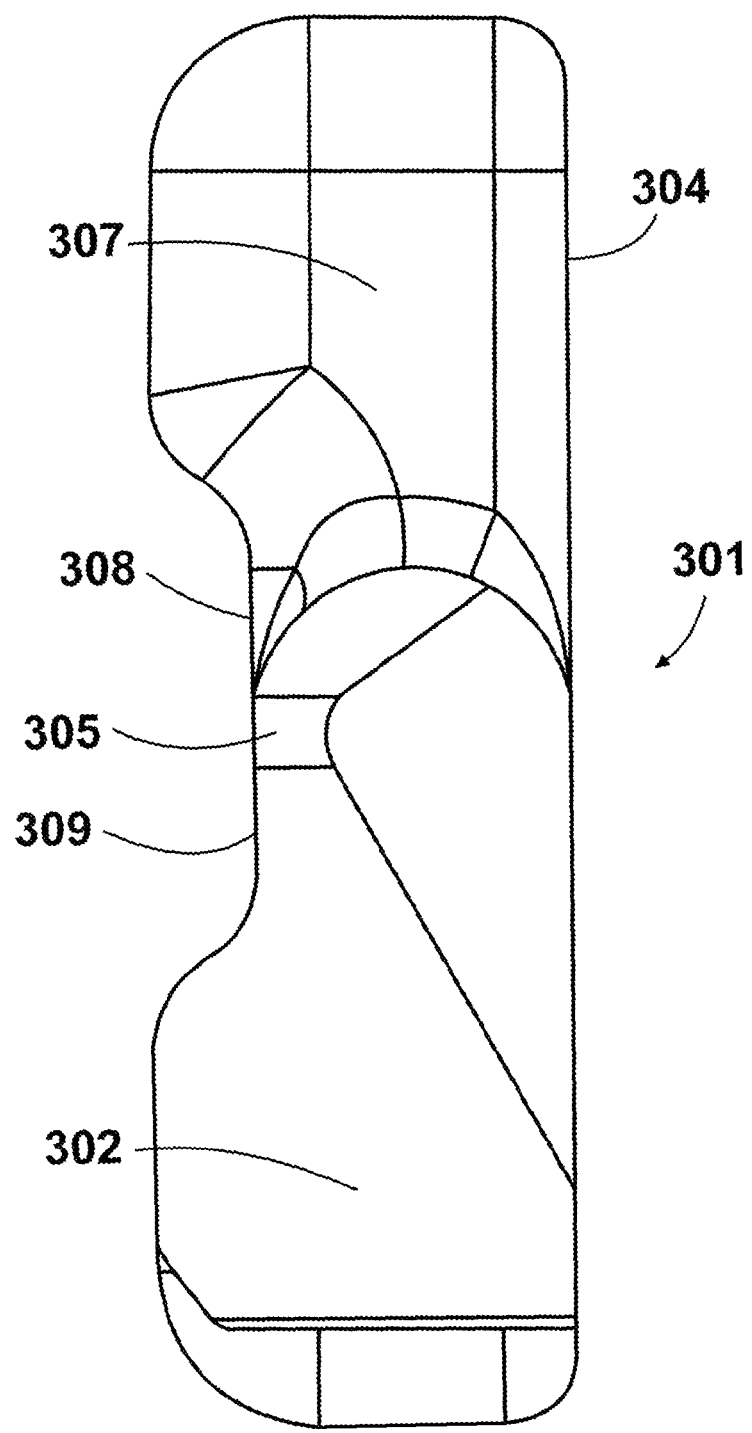

FIGS. 42A-46 present an embodiment which comprises a first (or push) ribbon 311 and a second (or guide) ribbon 310. Second ribbon 310 is configured to create an initial hole in the tissue (not shown) and to give an implant 301 stability during deployment. In FIG. 42 implant 301 comprises a stem or shaft 303 with a barb 302 on one side and a T-shaped section or crossbar 304 on the other side. This embodiment comprises a tapered end or point 305 proximal to barb 302. Point 305 can be used to help guide the implant 301 through tissue. Barb 302 comprises a capture surface or overhang 306 and a barb recess or trough 309. In this embodiment, crossbar 304 comprises two capture surfaces or faces 307 and a crossbar recess or trough 308. During installation and use, point 305 goes through the tissue until it emerges from the other side. The tissue is then held between the overhang 306 and the faces 307 with the aid of the shaft 303.

Figure 43:
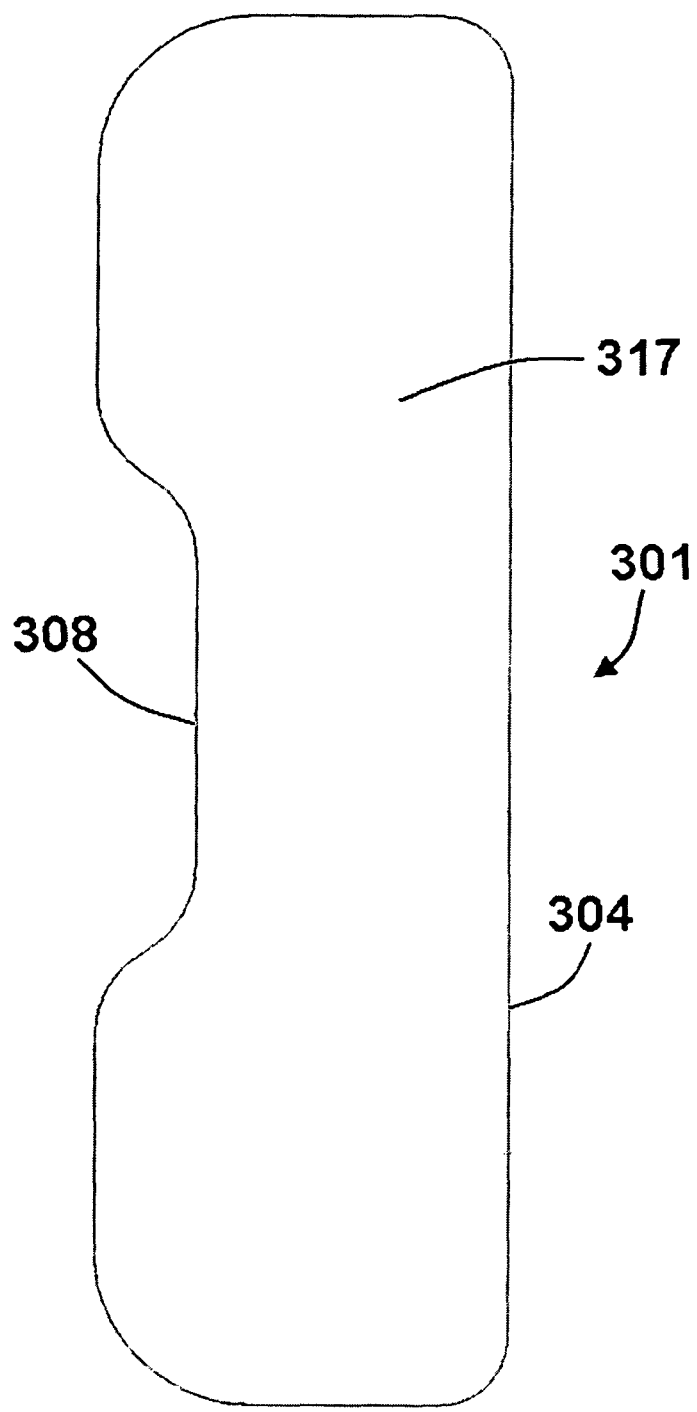
Figure 44:
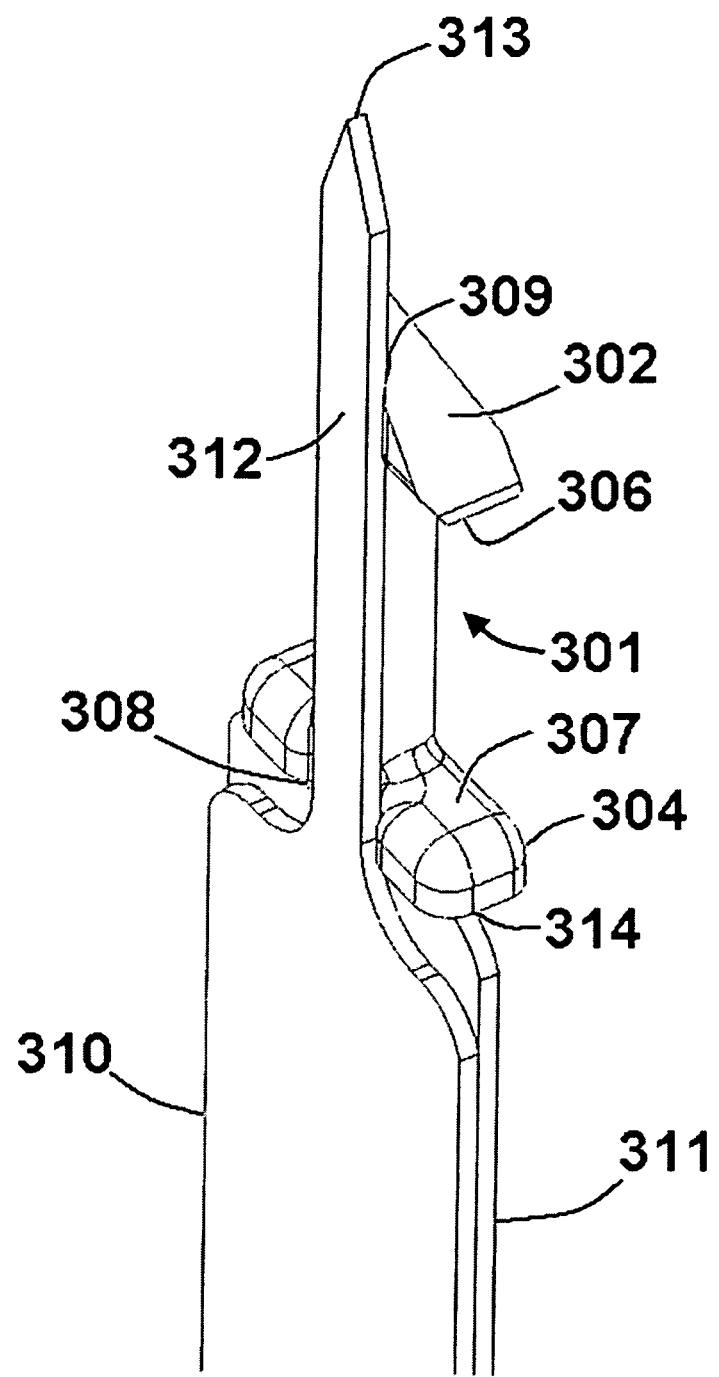

In the top view of the staple in FIG. 43, barb trough 309 and the crossbar trough 308 are more evident. The same is true for FIG. 44, which is the bottom view of implant 301.

Figure 45:
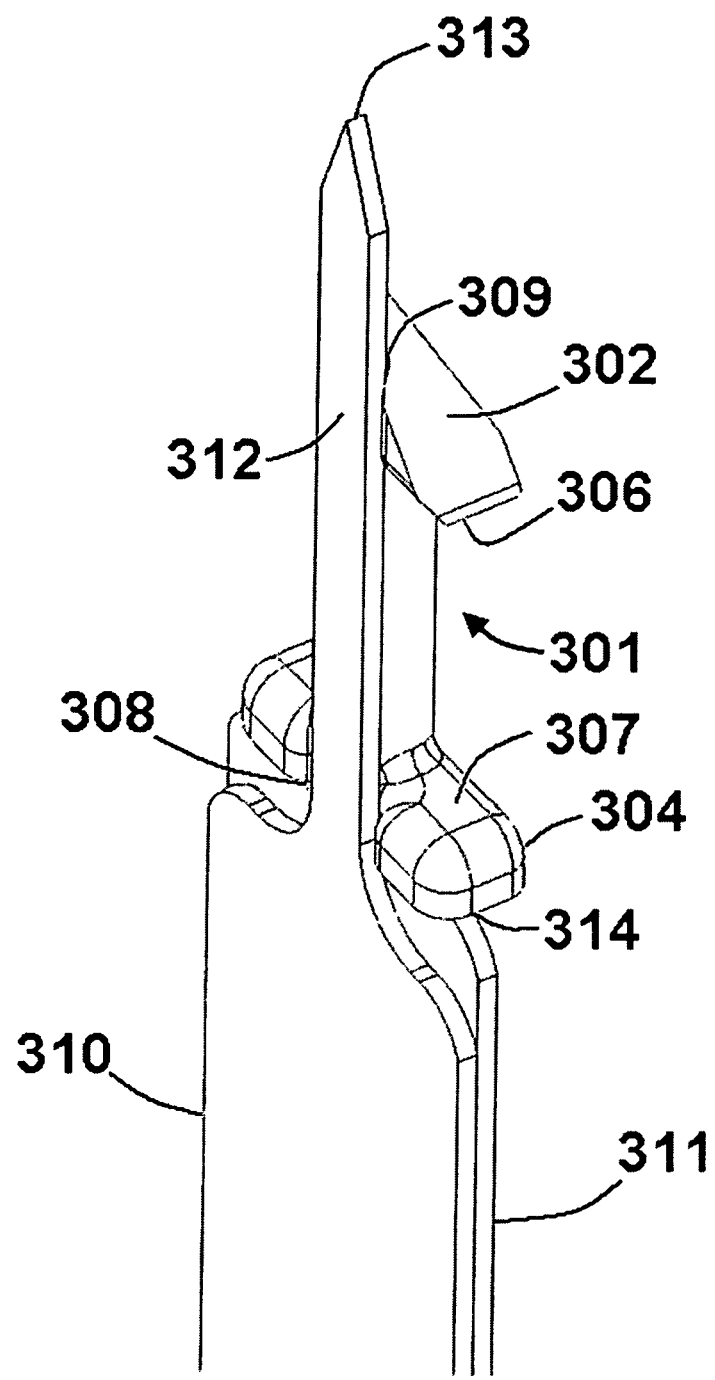
Figure 46:
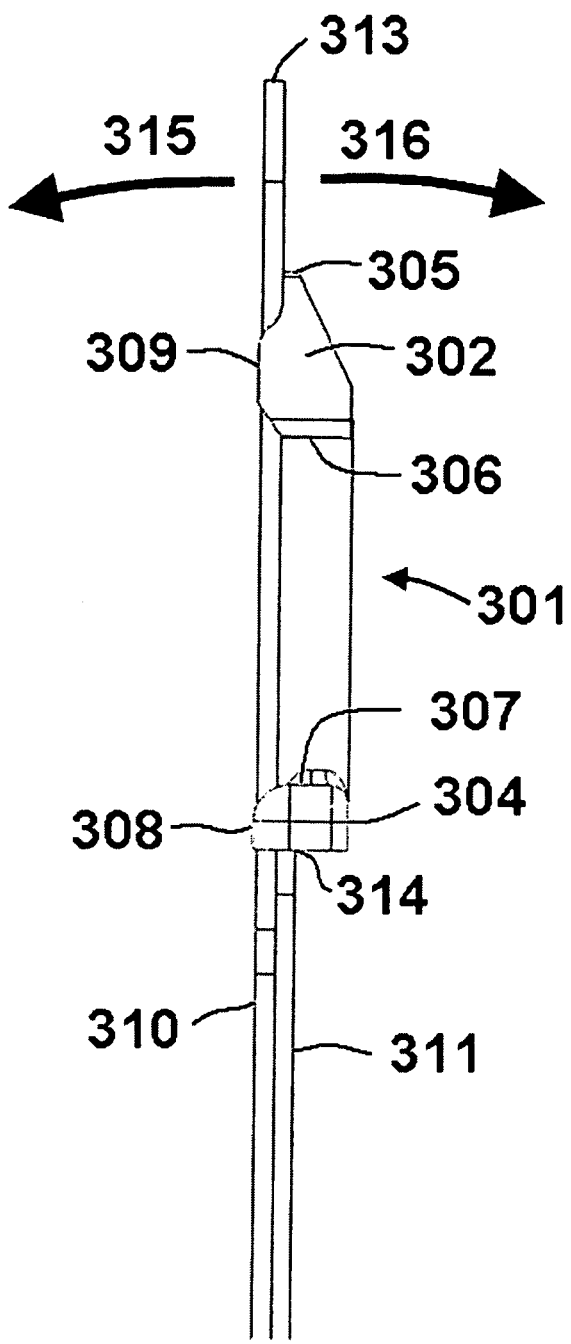

In FIGS. 45 and 46 implant 301 is shown in approximation to first ribbon 311 and second ribbon 310 as is the case when deploying implant 301. Second ribbon 310 has a narrowed section or extension 312 on the distal end with a tapered end or point 313 that initial pierces the tissue creating a leading hole for implant 301 to more easily pass through the tissue. First ribbon 311 has a flat edge 314 on the distal end that pushes against a lower surface 317 of the crossbar 304 in order to push the staple through the tissue.

Implant 301 is stabilized during the deployment phase in part by the first ribbon 311 and second ribbon 310. Extension 312 of first ribbon 310 engages crossbar trough 308 to keep the implant 301 from moving side to side (e.g. towards or away from the plane of the paper in FIG. 46). Extension 312 also fits into or engages barb trough 309 to restrict movement in one direction. Implant 301 is also constrained from rotating in one direction 315 by the rigidity of the implant 312, whereas implant 312 is constrained in the opposite direction 316 by a channel in the implant system (not shown in FIGS. 45-46, but shown as channel 57 in FIG. 47). First ribbon 311 comprises an engagement surface 314 that engages lower surface 317 during installation. In this embodiment, engagement surface 314 is a flat edge at one end of first ribbon 311. The engagement of these engagement surface 314 and lower surface 317 also tends to keep implant 301 in a stable, straight position during installation.

Figure 47:
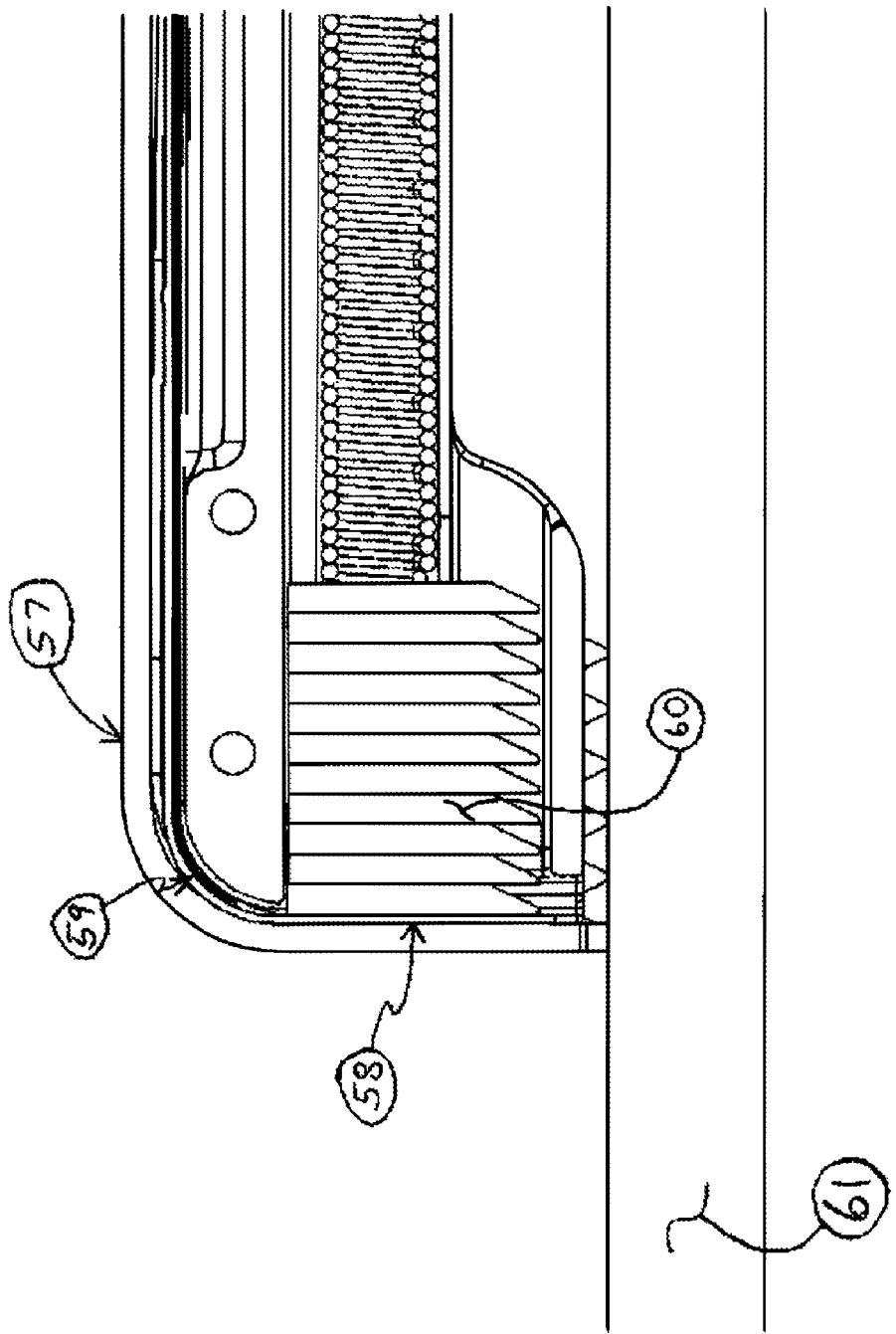
FIGS. 47-51 illustrate sectional views of a portion of an implant system.

A more detailed set of drawings describing the deployment method of exemplary embodiments is shown in FIGS. 47 to 51. In FIG. 47 the system at rest consists of a channel 57 enclosing a curved first ribbon 59 (shown in solid black heavier line weight) and a curved second ribbon 58. In certain embodiments, first ribbon 59 is similar to distal end 173 of actuator rod 165 in the embodiment described in FIGS. 1-12. In addition to the components described in FIGS. 1-12, the system shown in FIGS. 47-51 comprises second ribbon 58, which can further assist in placing an implant into a desired tissue location, as described in more detail below.

Figure 48:
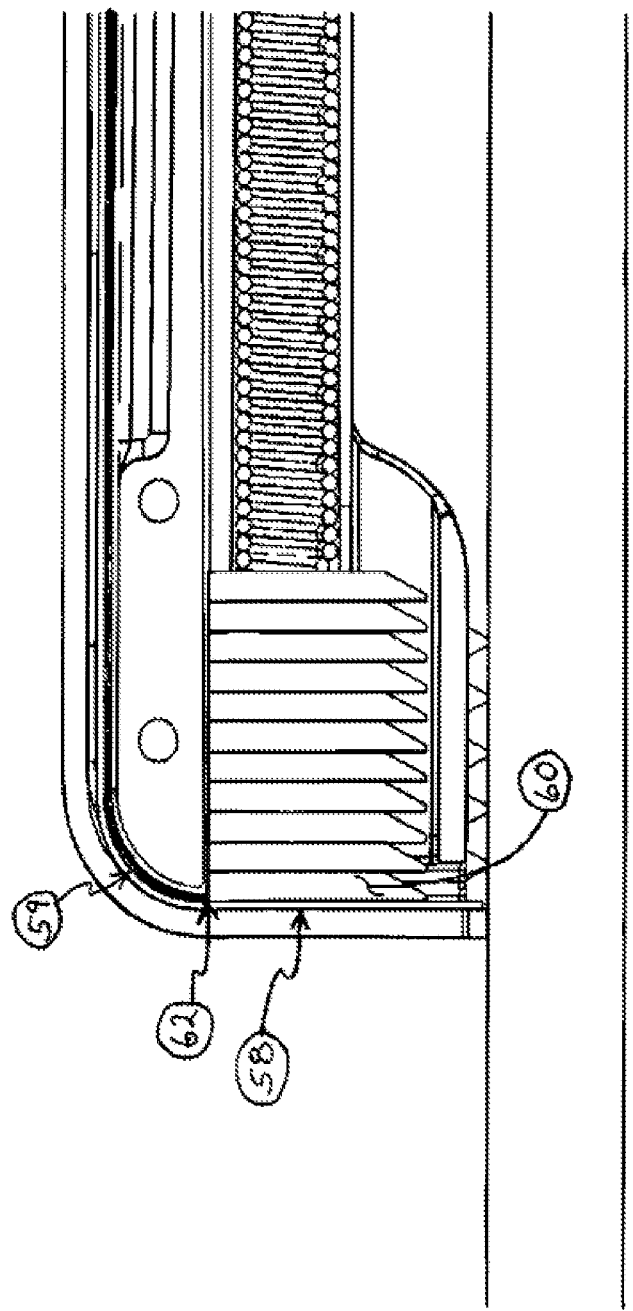
Figure 49:
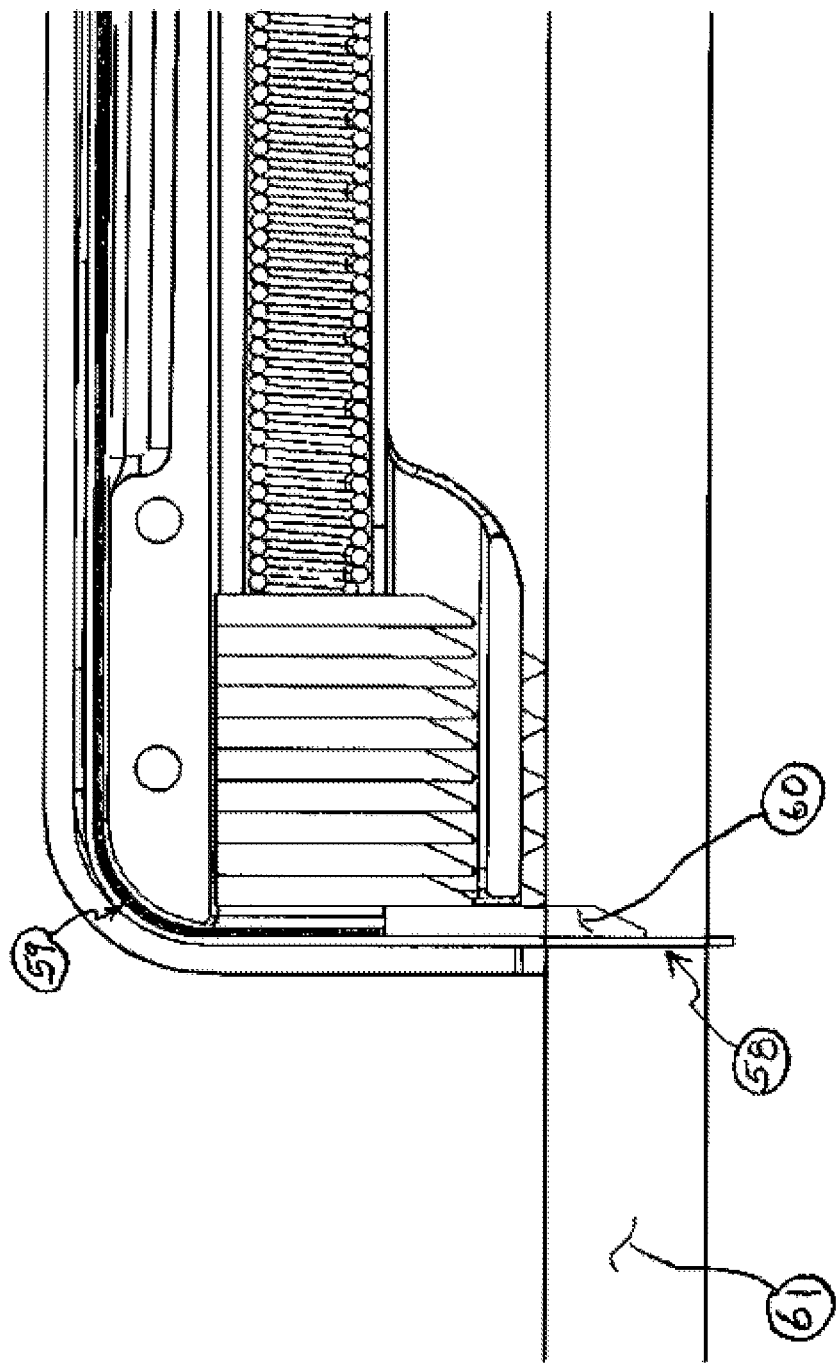
Figure 50:
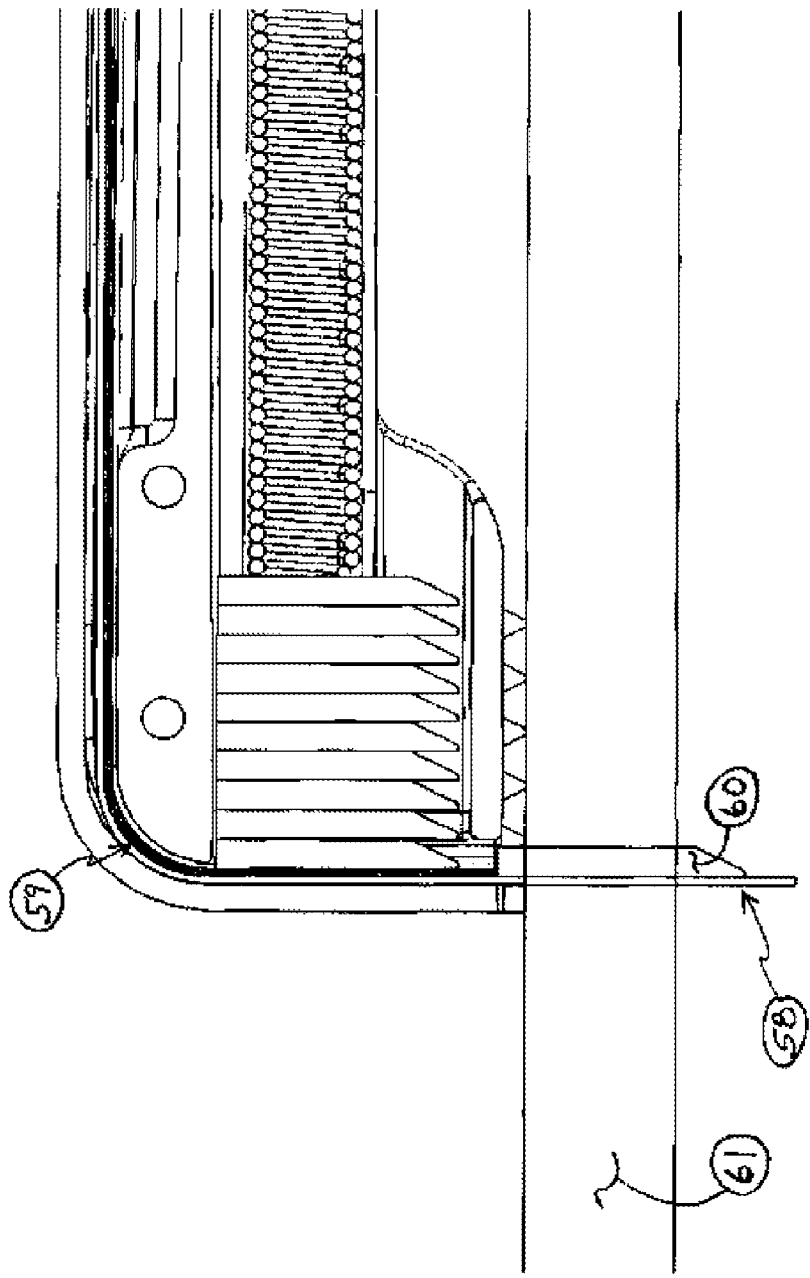
Figure 51:
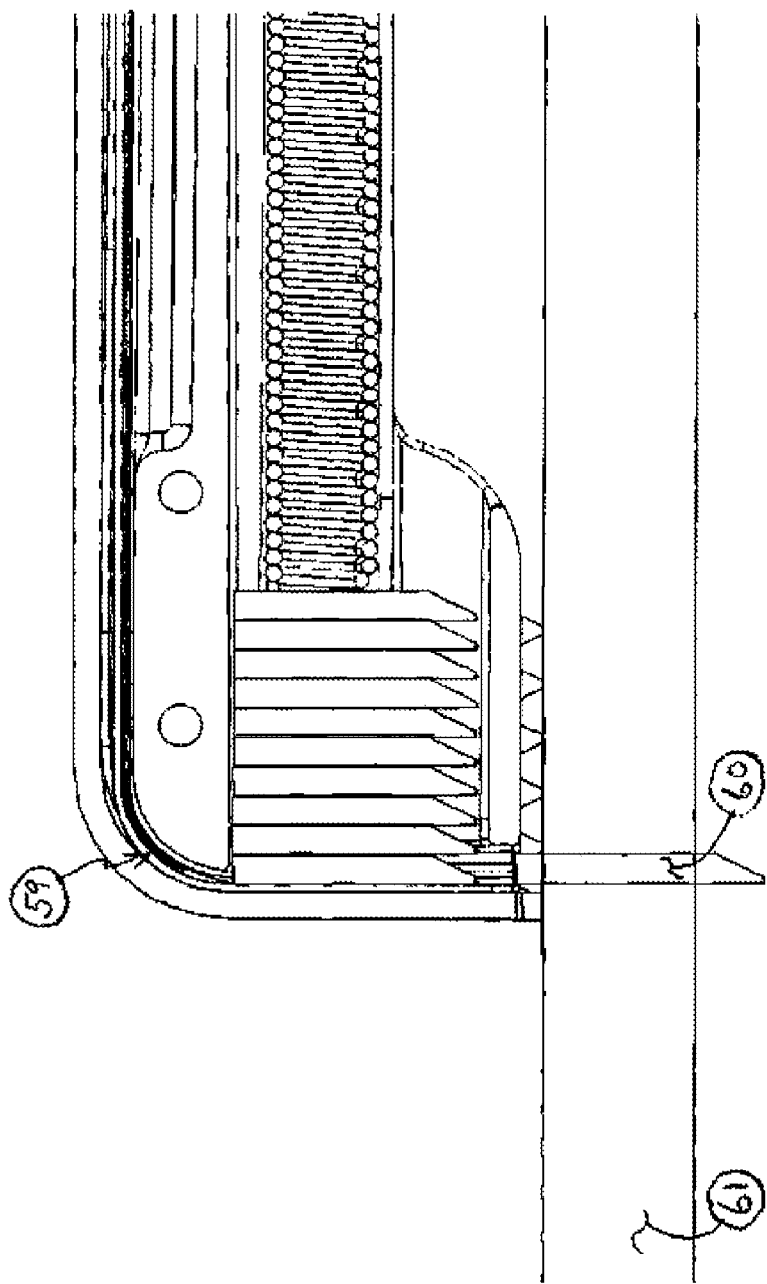

Also shown in the Figures are several implants 60 lined up ready for deployment. In the embodiments shown, channel 57 is resting against a layer of tissue 61. In FIG. 48, an actuator (not shown) has been partially actuated and ribbons 58 and 59 are beginning to deploy such that the distal end 62 of first ribbon 59 is in contact with a first implant 60. As shown in FIG. 49, when actuation of the actuator continues, the ribbons 58 and 59 are further deployed, with second ribbon 58 creating a hole in the tissue 61 and the first ribbon 59 beginning to push implant 60 through that hole. In FIG. 50, the actuator has been fully actuated and first and second ribbons 58 and 59 are fully deployed. Implant 60 is now in its installed position with the base portion and head portion on opposite sides of tissue 61. Although not visible in the cross-section views of FIGS. 47-51, implant 60 may comprise a T-shaped base portion on one side of tissue 61 and a barb or tissue-capturing head section on the opposite side of tissue 61 (when implant 60 is in its final installed location). As shown in FIG. 51, first and second ribbons 59 and 58 have been retracted to their original position in FIG. 51 leaving the implant 60 within the tissue 61. Implant 60 may comprise any of the disclosed embodiments (as well as variations thereof).

While exemplary embodiments are described herein, it will be understood that various modifications to the method and apparatus can be made without departing from the scope of the present invention. For example, different configurations of implants may be used. In specific embodiments, an implant may have an L-shaped portion rather than a T-shaped portion near its base. Furthermore, certain embodiments may not comprise implants in a cartridge arrangement. In addition, the implants may be used in procedures other than septoplasty. For example, any area where tissue approximation is necessary in an enclosed space such as peritoneal, urethral, bladder, GI tract, esophageal repair, or joint repair. Furthermore, the sequential recitation of steps in any claim is not a requirement that the steps be performed in any particular order, unless otherwise so stated.

The invention claimed is:

1. An implant system comprising:
a handle assembly comprising a handle and an actuator;
a first elongate arm having a first end and a second end coupled to the handle assembly;
a second elongate arm having a first end and a second end coupled to the handle assembly, the second elongate arm being movable between an open position substantially parallel to the first elongate arm and a closed position wherein the first end of the second elongate arm is closer to the first end of the first elongate; arm
a cartridge assembly coupled to and proximal to the first end of the first elongate arm, wherein the cartridge assembly comprises a plurality of implants;
wherein the actuator is configured to engage an actuator rod when the actuator is actuated and wherein the actuator rod comprises a flexible end proximal to the plurality of implants.

2. The implant system of claim 1, wherein the implant system is configured to discharge an implant from the cartridge assembly towards the second elongate arm when the actuator is actuated.

3. The implant system of claim 1, wherein:
the actuator comprises a trigger; and
the actuator rod is configured to discharge an implant when the actuator is actuated.

4. The implant system of claim 3, further comprising a biasing member configured to bias the actuator rod away from the first end of the first elongate arm.

5. The implant system of claim 3 wherein a portion of the actuator rod is configured to move generally parallel to the first elongate arm during use.

6. The implant system of claim 3 wherein the actuator rod comprises a ram configured to engage the actuator during use.

7. The implant system of claim 1 wherein the flexible end of the actuator rod is configured to engage an implant during use.

8. The implant system of claim 7, further comprising a guide that directs the flexible end of the actuator rod at an angle to the first elongate arm during use.

9. The implant system of claim 6, wherein the guide is proximal to the first end of the first elongate arm.

10. The implant system of claim 1, wherein the cartridge assembly is disposable.

11. The implant system of claim 1 wherein the implant system is configured to move the second elongate arm to the closed position when the actuator is actuated.

12. The implant system of claim 1, further comprising a cam gear having a cam surface engaged with the second elongate arm, wherein:
the actuator comprises an actuator gear engaged with the cam gear; and
actuation of the actuator causes the cam surface to move the second elongate arm.

13. The implant system of claim 1, further comprising an actuator having a cam surface engaged with the second elongate arm, wherein:
actuation of the actuator causes the cam surface to move the second elongate arm.

14. The implant system of claim 1 wherein the plurality of implants are comprised of an absorbable copolymer.

15. An implant system comprising:
a handle;
a first elongate arm having a proximal end coupled to the handle and a distal end, the distal end being configured to receive an implant;
a second elongate arm having a proximal end coupled to the handle and a distal end, the second elongate arm being movable between an open position substantially parallel to the first elongate arm and a closed position wherein the distal end of the second elongate arm is closer to the distal end of the first elongate arm;
an actuator coupled to the handle proximal to the proximal end of the first elongate arm, wherein the implant system is configured to move the second elongate arm between the first and second positions and discharge an implant from the distal end of the first elongate arm toward the second elongate arm at an angle to the first elongate arm when the actuator is actuated; and
an actuator rod between the actuator and the implant, wherein the actuator rod comprises a flexible end proximal to the implant.

16. The implant system of claim 15, wherein the angle is between 0 and 180 degrees.

17. The implant system of claim 15 wherein the angle is between 0 and 90 degrees.

18. The implant system of claim 15, wherein the angle is approximately 90 degrees.

19. The implant system of claim 15, wherein the angle is approximately 45 degrees.

20. A method for approximation of soft tissues, the method comprising:
providing an implant system comprising:
an elongate arm having a first end and a second end;
a cartridge assembly proximal to the first end, wherein the cartridge assembly comprises a plurality of implants;
an actuator configured to discharge an implant from the cartridge assembly; and an actuator rod between the actuator and the plurality of implants, wherein the actuator rod comprises a flexible end proximal to the implant;
inserting the elongate arm into a patient's nasal cavity;
locating the first end proximal to a target implant location;
actuating the actuator; and
discharging an implant into the target implant location.

21. An implant system comprising:
a first elongate arm having a first end and a second end;
an implant proximal to the first end;
a handle assembly proximal to the second end, wherein the handle assembly comprises a handle and an actuator;
a first actuator rod comprising a first flexible portion proximal to the first end, wherein the first flexible portion is configured to engage the implant; and
a second actuator rod comprising a second flexible portion proximal to the first end, wherein the second flexible portion comprises a first tip configured to penetrate tissue.

22. The implant system of claim 21 wherein upon partial actuation of the actuator:
the actuator is operatively engaged with the first and second actuator rods;
the first flexible portion of the first actuator rod is engaged with the implant; and
the second actuator rod is configured such that the first tip extends past the implant.

23. The implant system of claim 22 wherein upon full actuation of the actuator:
the actuator is operatively engaged with the first and second actuator rods;
the implant is discharged from the implant system; and
the second actuator rod is configured such that the first tip extends past the implant.

24. The implant system of claim 21 wherein the implant comprises a bevel proximal to the a distal end of the implant.

25. The implant system of claim 24 wherein the bevel directs the implant toward the second flexible portion when the implant is penetrating into tissue during use.

26. The implant system of claim 21 wherein the implant comprises an aperture and the second flexible portion is configured to extend through the aperture upon full actuation of the actuator.

27. The implant system of claim 21 wherein the implant comprises a slot and the second flexible portion is configured to extend through the slot upon full actuation of the actuator.

28. The implant system of claim 21 wherein the second flexible portion comprises a second tip.

29. The implant system of claim 28 wherein the second tip is configured to extend through an aperture or slot in the implant.

30. The implant system of claim 21 wherein the system is configured to discharge the implant at an angle to the first elongate arm.

31. The implant system of claim 21 wherein the implant is part of a cartridge assembly when the actuator is actuated.

32. The implant system of claim 21, further comprising a second elongate arm comprising a distal end and a proximal end.

33. The implant system of claim 32, wherein the second elongate arm is generally parallel to the first elongate arm when the actuator is not actuated.

* * * * *